(12) United States Patent
Doubet et al.

(10) Patent No.: US 11,446,450 B2
(45) Date of Patent: Sep. 20, 2022

(54) SYRINGE ADAPTER FOR MEDICATION

(71) Applicants: James T. Doubet, Parker, CO (US);
Paul D. Doubet, Farmington, IL (US)

(72) Inventors: James T. Doubet, Parker, CO (US);
Paul D. Doubet, Farmington, IL (US)

( * ) Notice: Subject to any disclaimer, the term of this patent is extended or adjusted under 35 U.S.C. 154(b) by 0 days.

(21) Appl. No.: 17/404,954

(22) Filed: Aug. 17, 2021

(65) Prior Publication Data

US 2021/0369980 A1 Dec. 2, 2021

Related U.S. Application Data

(60) Division of application No. 16/563,896, filed on Sep. 8, 2019, now abandoned, which is a
(Continued)

(51) Int. Cl.
*A61M 5/34* (2006.01)
*A61M 39/10* (2006.01)
*A61M 5/31* (2006.01)

(52) U.S. Cl.
CPC .......... *A61M 5/345* (2013.01); *A61M 5/3134* (2013.01); *A61M 39/1011* (2013.01); *A61M 2039/1033* (2013.01)

(58) Field of Classification Search
CPC .. A61M 5/345; A61M 5/3134; A61M 5/1782; A61M 5/204; A61M 2039/1033;
(Continued)

(56) References Cited

U.S. PATENT DOCUMENTS

| 822,079 A | 5/1906 | Roussy |
| 2,626,603 A | 1/1953 | Gabriel |

(Continued)

FOREIGN PATENT DOCUMENTS

| EP | 1923086 B1 | 4/2012 |
| KR | 20120107161 A | 10/2012 |

(Continued)

OTHER PUBLICATIONS

In re James T. Doubet, et al., U.S. Appl. No. 16/563,896, filed Sep. 8, 2019, Office Action, dated Jan. 10, 2020, 11 pages.
(Continued)

*Primary Examiner* — Kevin C Sirmons
*Assistant Examiner* — Alexandra Lalonde
(74) *Attorney, Agent, or Firm* — Marcia L. Doubet

(57) ABSTRACT

An improved apparatus for use with medication in a fluid form, which is particularly beneficial for medications having a relatively high viscosity. A disclosed syringe adapter has an opening that is relatively large, as compared to a conventional needle, and thus affixing the disclosed syringe adapter to a syringe improves syringeability of higher-viscosity medications. Some embodiments feature a lateral extension that prevents inserting the syringe adapter too far into a medicine bottle, and some embodiments feature a component that assists in firmly grasping. When the disclosed syringe adapter is affixed to a pistol-grip syringe or tab-handled syringe, the medication withdrawn into the pistol-grip syringe can be more easily administered a syringe barrel. In some embodiments, the syringe adapter will be replaced with a needle prior to injecting the medication, while in some other embodiments, the needle is affixed for the injection to the syringe adapter in place.

20 Claims, 10 Drawing Sheets

Related U.S. Application Data continuation-in-part of application No. 16/166,111, filed on Oct. 21, 2018, now Pat. No. 11,097,058, which is a continuation-in-part of application No. 16/010,155, filed on Jun. 15, 2018, now Pat. No. 11,337,894.

(58) Field of Classification Search
CPC .... A61M 39/1011; A61M 5/158; A61M 5/32; A61M 5/34; A61M 2005/2006; A61M 2005/3114; A61M 39/10; A61M 5/1413; A61M 5/344; A61M 5/347; A61M 2005/3142; A61M 2039/0009; A61M 2039/1016; A61M 2039/1077; A61M 2209/00; A61J 1/2096; A61J 1/2089; A61J 1/20; A61J 1/1406; A61J 1/2048; A61J 1/2055; A61J 1/2003; A61J 1/2051; A61J 1/2065; B01F 15/0225
See application file for complete search history.

(56) References Cited

U.S. PATENT DOCUMENTS

| | | | |
|---|---|---|---|
| 2,752,919 | A | 7/1956 | Gabriel |
| 3,320,954 | A | 5/1967 | Cowley |
| 3,436,828 | A | 4/1969 | Dragan |
| 3,958,570 | A | 5/1976 | Vogelman et al. |
| 4,046,145 | A | 9/1977 | Choksi et al. |
| 4,294,250 | A | 10/1981 | Dennehey |
| 4,316,462 | A | 2/1982 | Baker |
| 4,338,925 | A | 7/1982 | Miller |
| 4,472,141 | A | 9/1984 | Dragan |
| 4,664,655 | A | 5/1987 | Orentreich et al. |
| 4,758,158 | A | 7/1988 | Pierce et al. |
| 4,758,234 | A | 7/1988 | Orentreich et al. |
| 4,927,417 | A | 5/1990 | Moncada et al. |
| 5,047,021 | A | 9/1991 | Utterberg |
| 5,195,985 | A | 3/1993 | Hall |
| 5,322,510 | A | 6/1994 | Lindner et al. |
| 5,344,404 | A * | 9/1994 | Benson ............... A61M 5/3202 604/110 |
| 5,445,523 | A | 8/1995 | Fischer et al. |
| 5,509,911 | A | 4/1996 | Cottone, Sr. et al. |
| 5,733,258 | A | 3/1998 | Lane |
| 5,746,733 | A | 5/1998 | Capaccio et al. |
| 5,776,124 | A * | 7/1998 | Wald ...................... A61J 1/2096 604/403 |
| 5,924,584 | A * | 7/1999 | Hellstrom ............. A61J 1/2096 215/249 |
| 6,117,113 | A | 9/2000 | Novacek et al. |
| 6,511,472 | B1 | 1/2003 | Hayman et al. |
| 6,787,568 | B1 | 9/2004 | Mihalik |
| 6,790,867 | B2 | 9/2004 | Kohan et al. |
| 6,981,618 | B2 | 1/2006 | Reisinger |
| 7,347,458 | B2 | 3/2008 | Rome et al. |
| 7,472,932 | B2 | 1/2009 | Weber et al. |
| 7,682,343 | B2 | 3/2010 | Westbye |
| 7,699,609 | B2 | 4/2010 | Lawter et al. |
| 7,803,139 | B2 | 9/2010 | Fangrove, Jr. |
| 8,034,845 | B2 | 10/2011 | Freehauf et al. |
| 8,044,102 | B2 | 10/2011 | Kohan et al. |
| D736,915 | S | 8/2015 | Schultz |
| 9,295,788 | B2 | 3/2016 | Green |
| 9,801,788 | B2 | 10/2017 | Banik et al. |
| 10,709,850 | B2 | 7/2020 | Doubet et al. |
| 11,071,834 | B2 * | 7/2021 | Doubet ............... A61M 5/3293 |
| 11,090,444 | B2 | 8/2021 | Doubet et al. |
| 11,097,058 | B2 | 8/2021 | Doubet et al. |
| 11,173,257 | B2 | 11/2021 | Doubet |
| 2002/0173753 | A1 | 11/2002 | Caizza et al. |
| 2003/0236501 | A1 | 12/2003 | Donnan et al. |
| 2004/0039365 | A1 | 2/2004 | Aramata et al. |
| 2004/0068266 | A1 | 4/2004 | Delmotte |
| 2004/0116873 | A1 | 6/2004 | Fojtik |
| 2005/0159724 | A1 * | 7/2005 | Enerson ............... A61J 1/2096 604/411 |
| 2006/0047251 | A1 | 3/2006 | Bickford Smith et al. |
| 2006/0270996 | A1 | 11/2006 | Fojtik |
| 2006/0271015 | A1 | 11/2006 | Mantell |
| 2007/0060898 | A1 | 3/2007 | Shaughnessy et al. |
| 2007/0183986 | A1 | 8/2007 | Allred et al. |
| 2007/0203451 | A1 | 8/2007 | Murakami et al. |
| 2008/0015539 | A1 * | 1/2008 | Pieroni ............... A61J 1/2096 604/403 |
| 2008/0115796 | A1 | 5/2008 | Montanari et al. |
| 2008/0188816 | A1 | 8/2008 | Shimazaki et al. |
| 2008/0287884 | A1 | 11/2008 | Warden et al. |
| 2009/0182284 | A1 | 7/2009 | Morgan |
| 2009/0227894 | A1 | 9/2009 | Fojtik |
| 2011/0028909 | A1 | 2/2011 | Lum et al. |
| 2012/0130317 | A1 | 5/2012 | Thorley |
| 2012/0184938 | A1 | 7/2012 | Lev et al. |
| 2012/0265163 | A1 * | 10/2012 | Cheng ................ A61J 1/2096 604/415 |
| 2013/0018354 | A1 | 1/2013 | Sund et al. |
| 2013/0178806 | A1 | 7/2013 | Felix-Faure et al. |
| 2013/0331810 | A1 | 12/2013 | Bazala et al. |
| 2014/0066840 | A1 | 3/2014 | Mantell |
| 2014/0261860 | A1 | 9/2014 | Heath et al. |
| 2017/0165192 | A1 | 6/2017 | Georges et al. |
| 2017/0203086 | A1 | 7/2017 | Davis |
| 2018/0050183 | A1 * | 2/2018 | Taylor ................. A61M 39/20 |
| 2018/0104150 | A1 * | 4/2018 | Dubaele ............. A61J 1/2096 |
| 2018/0344570 | A1 | 12/2018 | Davis et al. |

FOREIGN PATENT DOCUMENTS

| | | |
|---|---|---|
| KR | 10-2047319 B1 | 11/2019 |
| WO | WO2004/096326 A1 | 11/2004 |
| WO | 2012/023955 A1 | 2/2012 |
| WO | 2014145959 A1 | 9/2014 |
| WO | 2017/091643 A1 | 6/2017 |

OTHER PUBLICATIONS

In re James T. Doubet, U.S. Appl. No. 16/393,696, filed Apr. 24, 2019, Office Action, dated Jan. 10, 2020, 16 pages.
Colomer, S., et al., "Syringeability and Viscosity Comparative of Different Florfenicol Formulations", publication date unknown, printed from http://marketing.hipra.com/SELECTNEWS/trials/Syringeabiliy_viscosity_comparative_of_FLORFENICOL_formulations.pdf on May 14, 2018. 1 page.
In re James T. Doubet, U.S. Appl. No. 16/393,696, filed Apr. 24, 2019, Office Action, dated Jun. 27, 2019, 17 pages.
"List of Patents or Patent Applications to be Treated as Related". Jan. 30, 2022. 2 pages.
PCT Application PCT/US2019/036774, International Search Report dated Sep. 16, 2019 (2 pages).
PCT Application PCT/US2019/036774, Written Opinion of the International Searching Authority dated Sep. 16, 2019 (5 pages).
In re James T. Doubet, et al., U.S. Appl. No. 16/698,471, filed Nov. 27, 2019, Office Action, dated Jan. 10, 2020, 14 pages.
In re James T. Doubet, et al., U.S. Appl. No. 16/166,111, filed Oct. 21, 2018, Office Action, dated Sep. 4, 2020, 20 pages.
In re James T. Doubet, et al., U.S. Appl. No. 16/203,858, filed Nov. 29, 2018, Office Action, dated Sep. 22, 2020, 25 pages.
In re James T. Doubet, et al., U.S. Appl. No. 16/563,896, filed Sep. 8, 2019, Office Action, dated Aug. 27, 2020, 21 pages.
PCT Application PCT/US2019/062926, International Search Report dated Feb. 12, 2020 (2 pages).
PCT Application PCT/US2019/062926, Written Opinion of the International Searching Authority dated Feb. 12, 2020 (6 pages).
PCT Application PCT/US2019/056282, International Search Report dated Jan. 7, 2020 (2 pages).
PCT Application PCT/US2019/056282, Written Opinion of the International Searching Authority dated Jan. 7, 2020 (5 pages).
In re James T. Doubet, et al., U.S. Appl. No. 16/166,111, filed Oct. 21, 2018, Office Action, dated Apr. 3, 2020, 21 pages.

(56) References Cited

OTHER PUBLICATIONS

In re James T. Doubet, et al., U.S. Appl. No. 16/203,858, filed Nov. 29, 2018, Office Action, dated Apr. 3, 2020, 22 pages.
In re James T. Doubet, et al., U.S. Appl. No. 16/563,896, filed Sep. 8, 2019, Office Action, dated Jan. 14, 2021, 22 pages.
In re James T. Doubet, et al., U.S. Appl. No. 16/203,858, filed Nov. 29, 2018, Office Action, dated Jan. 21, 2021, 17 pages.
In re James T. Doubet, et al., U.S. Appl. No. 16/166,111, filed Oct. 21, 2018, Office Action, dated Jan. 11, 2021, 22 pages.
PCT Application PCT/US2019/036774, International Preliminary Report on Patentability dated Dec. 15, 2020 (6 pages).
PCT Application PCT/US2020/061523, International Search Report dated Feb. 9, 2021 (3 pages).
PCT Application PCT/US2020/061523, Written Opinion of the International Searching Authority dated Feb. 9, 2021 (8 pages).
PCT Application PCT/US2020/048978, International Search Report dated Nov. 10, 2020 (2 pages).
PCT Application PCT/US2020/048978, Written Opinion of the International Searching Authority dated Nov. 10, 2020 (6 pages).
In re James T. Doubet, et al., U.S. Appl. No. 16/895,370, filed Jun. 8, 2020, Office Action, dated Feb. 8, 2021, 22 pages.
In re James T. Doubet, et al., U.S. Appl. No. 16/563,896, filed Sep. 8, 2019, Office Action, dated May 18, 2021, 25 pages.
In re James T. Doubet, et al., U.S. Appl. No. 16/563,896, filed Sep. 8, 2019, Advisory Action, dated Jun. 21, 2021, 3 pages.
In re James T. Doubet, et al., U.S. Appl. No. 16/895,370, filed Jun. 8, 2020, Office Action, dated Oct. 15, 2020, 25 pages.

* cited by examiner

SECTION B-B

Exploded View

FIG. 15

|  | withdraw | expel |
|---|---|---|
| Test #1 | | |
| 18 gauge needle | 3 minutes 50.30 seconds | 35 seconds |
| 16 gauge needle | 35 seconds | 11 seconds |
| syringe adapter | 8 seconds | ---- |
| | | |
| Test #2 | | |
| syringe adapter | 5.54 seconds** | |
| | | |
| Test #3 | | |
| 16 gauge needle | 3 minutes 42.27 seconds | |
| syringe adapter | 1 minute 1 second | |

**Note: averaged over 5.76, 5.11, 4.64, 5.41, 5.97, 5.45 seconds after discarding 4.64 as an outlier

SYRINGE ADAPTER FOR MEDICATION

BACKGROUND

The present invention relates to improved apparatus for use with medication, and method(s) of using same, particularly for higher-viscosity medication.

Medication is needed for various purposes, including illness treatment and illness prevention.

BRIEF SUMMARY

The present invention is directed to improved apparatus for use with medication, and method(s) of using same, and is particularly useful for medication having a relatively high viscosity. In one aspect, a syringe adapter for withdrawing fluid medication from a container comprises a sidewall extending between a proximal end and a distal end, the sidewall having an interior surface defining a chamber, the proximal end configured to be connected to a syringe while withdrawing at least a portion of the fluid medication from the container through the chamber and into a barrel of the syringe and the distal end configured for inserting into the container for the withdrawal, wherein an opening at the distal end is relatively large in diameter to facilitate withdrawing fluid medication having a relatively high viscosity and the syringe adapter is configured to be removed from the syringe and replaced with a needle prior to subsequently injecting (for example, into an animal) the fluid medication (or at least some portion thereof) withdrawn into the barrel. The relatively large opening is directed toward improved syringeability of the fluid medication. The viscosity of the fluid medication is preferably greater than or equal to 50 centipoise units when a temperature of the fluid medication is at least 5 degrees Celsius.

The syringe is preferably configured as a pistol-grip syringe or a tab-handled syringe, and may therefore provide improved leverage for the subsequent injection. In an embodiment, the diameter of the opening at the distal end of the syringe adapter is preferably about 0.05 inches to about 0.1585 inches, and even more preferably, is about 0.09 inches to about 0.11 inches, and generally, is approximately 0.10 inches. In an embodiment, the sidewall is approximately 0.05 inches in thickness at the distal end. Optionally, the syringe adapter further comprises a flanged area that extends laterally from the proximal end. Optionally, the syringe adapter may further comprise a radial extension member that extends perpendicularly and radially outward from an exterior surface of the syringe adapter. In an embodiment, an outer shape of the syringe adapter is generally conical in a first portion and generally cylindrical in a second portion. In an embodiment, an inner shape of the syringe adapter, for at least a portion of the proximal end, is generally conical. In an embodiment, the inner shape of the syringe adapter tapers from the proximal end toward the distal end, for at least a portion of the proximal end, at approximately 6 percent. The syringe adapter preferably connects to the syringe using a Luer-type connection, the Luer-type connection selected from the group consisting of a Luer-type lock and a Luer-type slip.

In another aspect, a method of administering fluid medication (for example, to an animal) comprises: affixing a syringe adapter to a syringe, the syringe adapter comprising a sidewall extending between a proximal end and a distal end, the sidewall having an interior surface defining a chamber, the proximal end configured to be connected to a distal end of the syringe; inserting the distal end of the syringe adapter into a container of fluid medication having a relatively high viscosity; withdrawing, from the container, at least a portion of the fluid medication through the chamber and into a barrel of the syringe, wherein an opening at the distal end of the syringe adapter is relatively large in diameter to facilitate withdrawing the relatively-high-viscosity medication; removing the syringe adapter from the syringe subsequent to the withdrawing; affixing a needle to the distal end of the syringe, subsequent to the removing; and injecting (for example, into an animal) the fluid medication (or at least some portion thereof) previously withdrawn into the barrel.

In yet another aspect, the syringe adapter is configured for receiving a needle at its distal end, such that the needle is affixed to the distal end of the syringe adapter subsequent to withdrawing fluid medication into the barrel of the syringe, and the syringe adapter is configured to remain in place while injecting the fluid medication (or at least some portion thereof) into a recipient with the needle. In this aspect, administering the fluid medication may be repeated (for example, for another recipient) by removing the needle, using the in-place syringe adapter for withdrawing more fluid medication (from the same or a different container), re-affixing the needle to the syringe adapter, and then injecting this medication (or some portion thereof). In this aspect, the distal end of the syringe adapter preferably provides for a Luer-type connection with the needle, and the proximal end of the syringe adapter is preferably configured with a Luer-type locking member for connecting to the syringe. The syringe adapter may further comprise an extension member that extends perpendicularly outward from an exterior surface of the syringe adapter.

In still another aspect, a syringe adapter for withdrawing viscous fluid medication from a container comprises a sidewall extending between a proximal end and a distal end opposite the proximal end, the sidewall having an interior surface defining a chamber, a first opening at the distal end being defined by a first end of the sidewall and a second opening at the proximal end being defined by a second end of the sidewall. Preferably, the proximal end is configured to be connected to a distal end of a syringe, the distal end of the syringe having a third opening; the distal end of the syringe adapter is configured to be inserted into a container of viscous fluid medication; the first opening provides for fluid communication of the viscous fluid medication between the container and the chamber; the second opening provides for fluid communication of the viscous fluid medication between the chamber and, through the third opening, into the barrel; and the first opening has an inner diameter sized to facilitate withdrawing at least a portion of the viscous fluid medication through the first opening and into the chamber and then into the barrel. Preferably, at least a portion of the viscous fluid medication is caused to be withdrawn from the container, through the first opening and into the chamber, and then through the second and third openings into the barrel, upon activation of a drawing mechanism of the syringe while the proximal end of the syringe adapter is connected to the syringe and while the distal end of the syringe adapter is inserted into the container.

In a further aspect, a method of withdrawing viscous fluid medication from a container comprises: affixing a syringe adapter to a syringe, the syringe adapter comprising a sidewall extending between a proximal end and a distal end opposite the proximal end, the sidewall having an interior surface defining a chamber, a first opening at the distal end being defined by a first end of the sidewall and a second opening at the proximal end being defined by a second end of the sidewall, the proximal end configured to be connected to a distal end of the syringe; inserting the distal end of the syringe adapter into a container of viscous fluid medication; and withdrawing, from the container, at least a portion of the viscous fluid medication through the first opening and into the chamber, and from the chamber through the second opening and then through a third opening in the distal end of the syringe and into a barrel of the syringe, wherein the first opening has an inner diameter sized to facilitate the withdrawing. In this aspect, the syringe adapter is preferably configured to be removed from the syringe subsequent to the withdrawing and replaced by affixing a needle to the distal end of the syringe to thereby enable injecting, into a recipient with the needle, at least a portion of the viscous fluid medication withdrawn into the barrel.

Various embodiments of these and other aspects of the present invention may be provided in view of the present disclosure. It should be noted that the foregoing is a summary and thus contains, by necessity, simplifications, generalizations, and omissions of detail; consequently, those of ordinary skill in the art will appreciate that the summary is illustrative only and is not intended to be in any way limiting. Other aspects, inventive features, and advantages of the present invention, as defined by the appended claims, will become apparent in the non-limiting detailed description set forth below.

BRIEF DESCRIPTION OF THE SEVERAL VIEWS OF THE DRAWINGS

The present invention will be described with reference to the following drawings, in which like reference numbers denote the same element throughout.

FIG. 15 presents tables containing measurements from tests conducted to compare use of a sample version of the disclosed syringe adapter to use of conventional needles.

DETAILED DESCRIPTION

Figure 1:
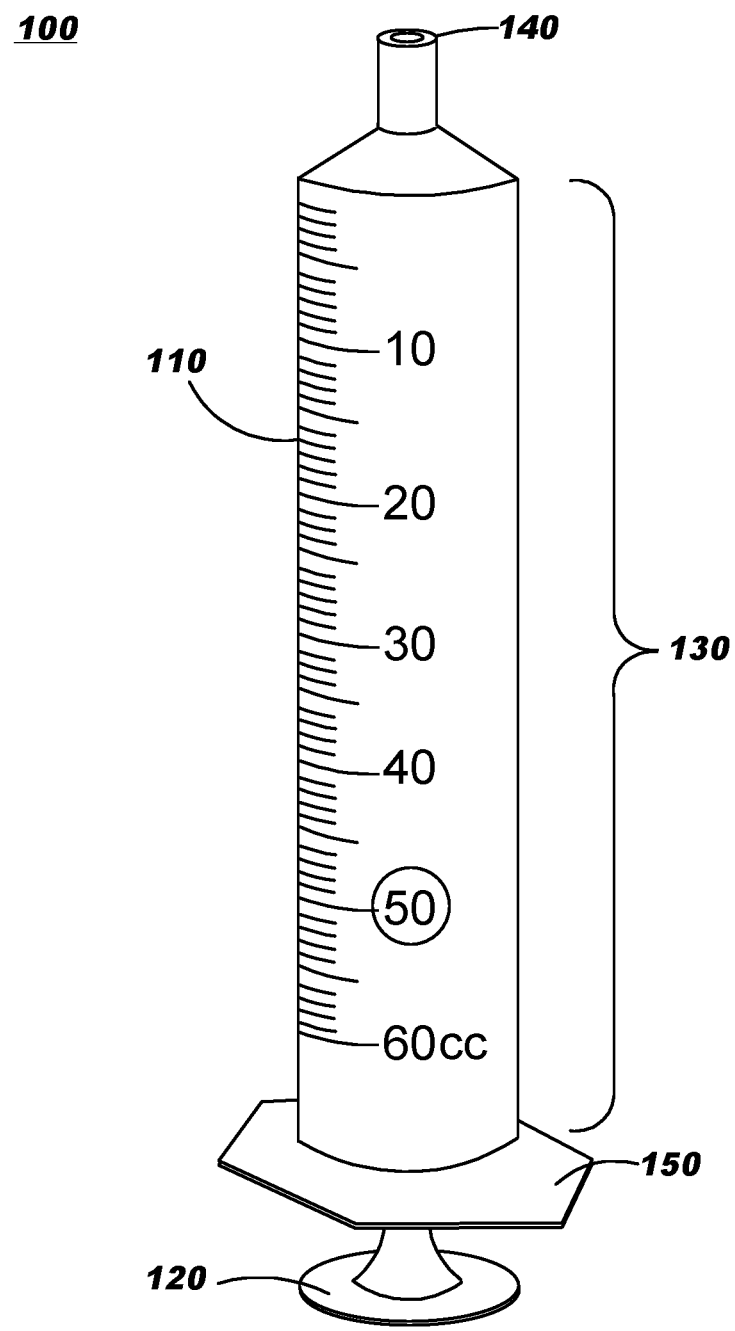
FIGS. 1-3 depict examples of prior art syringes.

As noted earlier, medication is needed for various purposes, including illness treatment and illness prevention. Discussions are presented herein with reference to medication used for animals, primarily in terms of livestock animals; this is by way of illustration and not of limitation, however, and it should be noted that the disclosed syringe adapter may be beneficial with medication used for all types of animal life, including humans.

Treatment of animals using medication may be desired whether the animal is a family pet, part of a livestock operation, is the subject of research, and so forth. Examples of medicating animals for illness treatment will be obvious, and may span a wide variety of illnesses. One example of medicating an animal for illness prevention is a proactive vaccination; another example is to proactively administer an antibiotic. In a commercial livestock operation, animals may be proactively medicated before they are introduced into another group of livestock, for example to guard against introducing an illness that they may carry or simply to ensure that all animals in the group have received an identical medication regimen. Medication might also be administered in anticipation of, or in response to, a change in weather conditions or a change in geographical location for an animal (such as moving from one climate to another). Hereinafter, animal medications are discussed without differentiation of the purpose for such medication.

Medication may be found in various forms, including solid and fluid. Solid substances may be ingestible, for example, while fluids may be injectable or may be administered orally or nasally. Embodiments of the present invention are directed toward improved apparatus for use with medication in fluid form, and the scope of the present invention also includes method(s) for using such apparatus.

Medications provided in fluid form may vary widely in their viscosity, depending upon their chemical formulation. Viscosity is sometimes defined as the resistance of a substance to flow. The viscosity of water is relatively low, for example, while the viscosity of honey is relatively high. The viscosity of some substances can be changed by applying heat; for example, melting butter increases its ability to flow. Some fluid medications may have a viscosity that is relatively low and is similar to that of water, for example, and thus will flow quite easily. Other fluid medications are known that have a viscosity that is markedly different from water.

Fluid medications intended for use with animals are commonly marketed in multi-dose packaging, such as bottles that hold enough fluid for administering several doses. A bottle of medication might hold 500 milliliters, for example (equivalently, 500 cubic centimeters), which is roughly equivalent to 16.9 ounces. The bottle might be made of glass or plastic, and a container having a configuration other than a bottle might be used. Hereinafter, the term "bottle" is used for ease of reference, and by way of illustration and not of limitation, as a container type in which medication may be contained.

One reason for marketing animal medication in multi-dose bottles is economic. The cost of the medication may be reduced, for example, by selling a larger quantity container and thereby reducing the relative cost of the packaging. Another reason for marketing animal medication in multi-dose bottles is that the dosage of many (if not all) medications is prescribed with regard to the animal's body weight. Accordingly, the correct amount of medication to use on a particular animal can be calculated and then withdrawn from the multi-dose bottle, after which it may be injected into the animal, and the remaining medication is then available for subsequent use.

A multi-dose bottle of fluid medication is typically marketed with a rubber membrane covering at least a portion of an opening at the top of the bottle. Conventionally, the fluid medication is withdrawn from such bottle by placing a needle onto the tip of a syringe, inserting a tip of the needle into the rubber membrane, and withdrawing a plunger of the syringe until an appropriate amount of fluid is pulled into the syringe body (referred to herein as the syringe "barrel"); this same needle is then used for injecting the medication from the syringe into the animal. FIG. 1 shows an example of a prior art syringe 100, and illustrates how the hollow barrel 130 of syringe 100 is commonly marked with fill lines 110 that are provided for measuring the amount of fluid contained therein. A needle is placed over (or inside) the tip 140, and fluid enters through an opening or eye of the needle and into the syringe barrel 130. The syringe includes a retractable plunger, a terminal end of which is shown at 120. (As will be obvious, as fluid medication is withdrawn from the bottle into the barrel 130, the plunger 120 movably extends outward from the proximal end of the syringe 100, although this is not illustrated in FIG. 1.) Commonly, a syringe as illustrated in FIG. 1 is constructed of plastic, making it relatively cheap to purchase.

A tab-shaped member 150 is also provided on syringe 100. When administering the medication from the barrel 130, a person's index finger is placed on the tab-shaped member 150 at one side of barrel 130 and the person's middle finger is placed on the tab-shaped member 150 at the opposing side of barrel 130, and the person's thumb is then used to depress the terminal end of plunger 120 into the barrel in order to expel the medication from the barrel.

Figure 2:
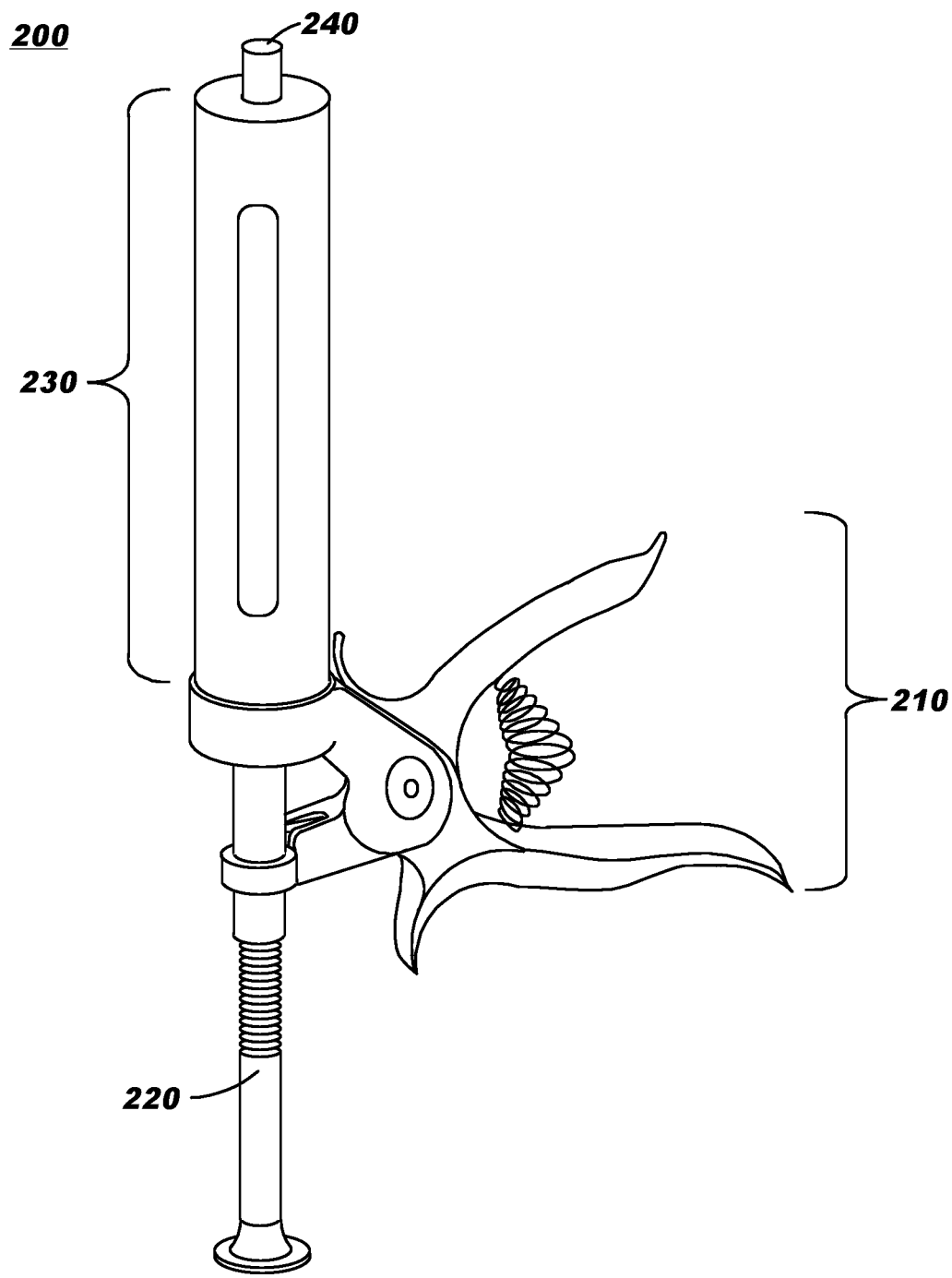

As an alternative to the syringe 100 of FIG. 1, an example of a so-called "pistol-grip" syringe is illustrated in FIG. 2. Fluid medication is drawn into a syringe of this type by pulling plunger 220 outwardly from the barrel 230. A tab-shaped member is not provided on a syringe of this type, as compressing or squeezing the handles 210 serves to expel medication from the barrel of a syringe having a pistol-grip configuration.

Figure 3:
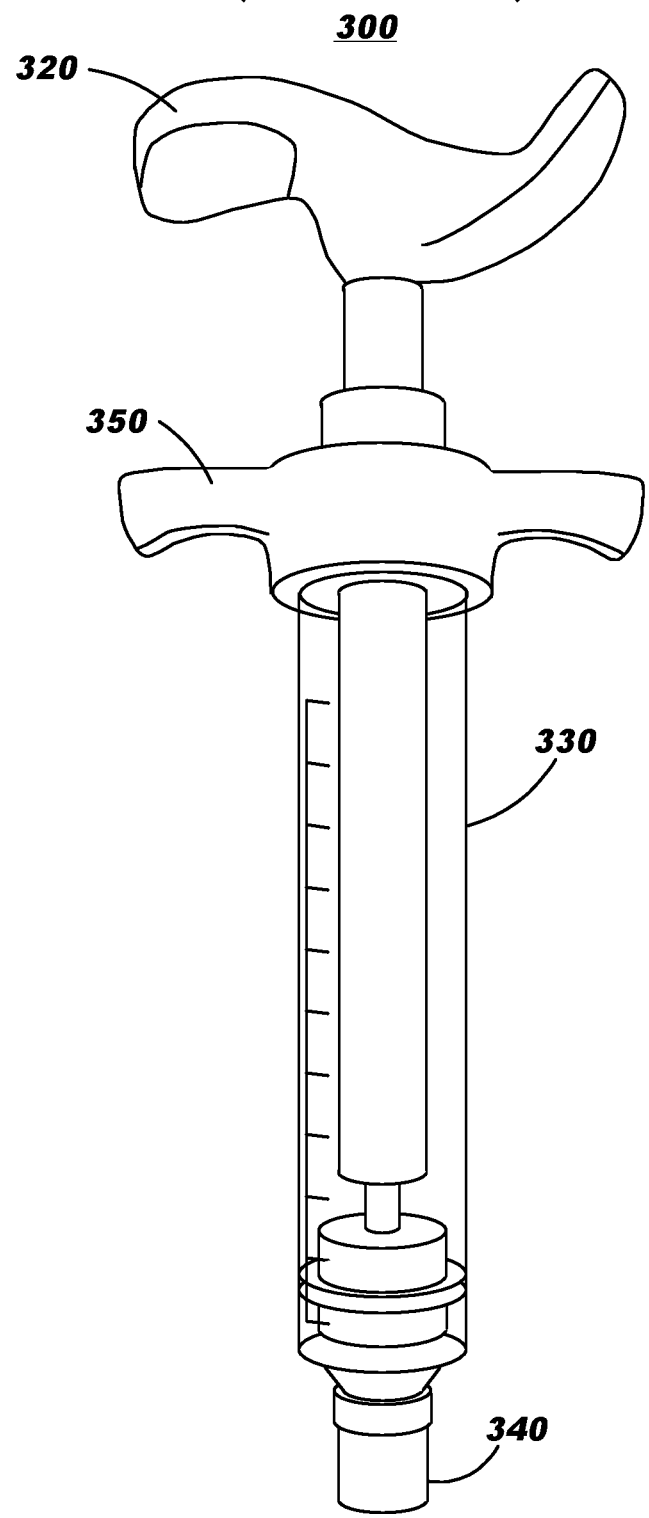

FIG. 3 illustrates yet another prior art syringe 300, and is referred to herein as a "tab-handled" syringe. In this configuration, the syringe has a tabbed member 350 near the proximal end of barrel 330, and includes a handle-style tabbed member 320 affixed to the terminal end of the plunger. The tabbed member 350 is used in a similar manner to tab-shaped member 150 of FIG. 1, whereby a person places fingers on the tabbed member 350 on opposing sides of barrel 330; the person then presses down on tabbed member 320 using the person's palm to depress the terminal end of the plunger into the barrel in order to expel the medication from the barrel. As will be readily understood, fluid medication is drawn into a syringe of this type by pulling handle 320 to thereby draw the attached plunger outwardly from the barrel 330. As compared to tab-shaped member 150 and plunger end 120 of FIG. 1, the tabbed members 320, 350 of FIG. 3 typically provide improved comfort for the person using the tab-handled syringe.

Figure 14A:
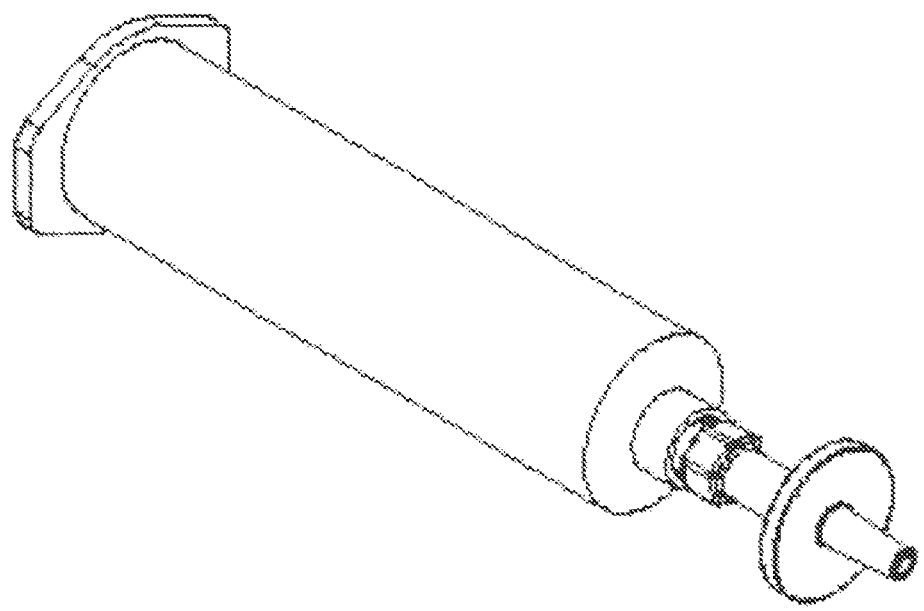
FIG. 14 (comprising FIGS. 14A through 14D) illustrates a further embodiment of the disclosed syringe adapter, showing exterior views as well as cross-sectional views of placement thereof upon a syringe and as exploded.
Figure 14B:
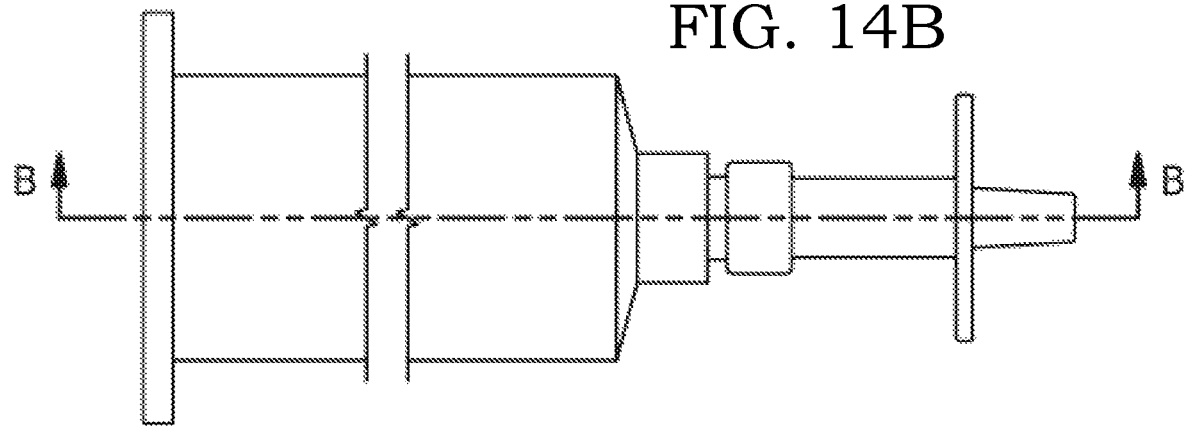
Figure 14C:
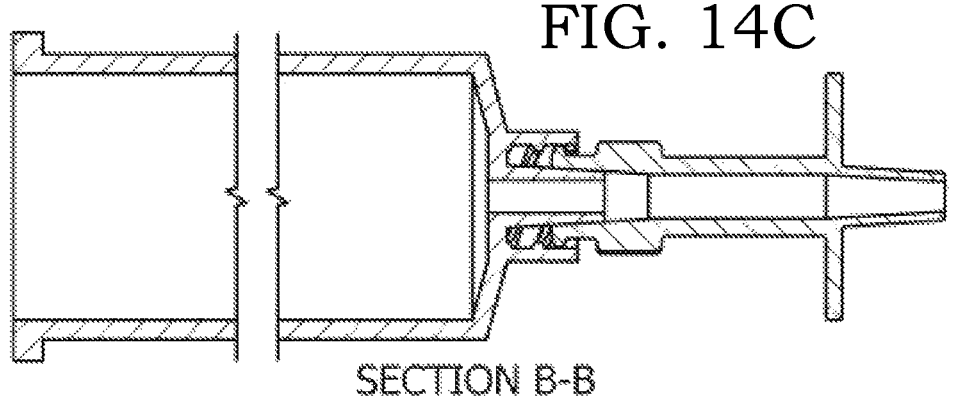
Figure 14D:
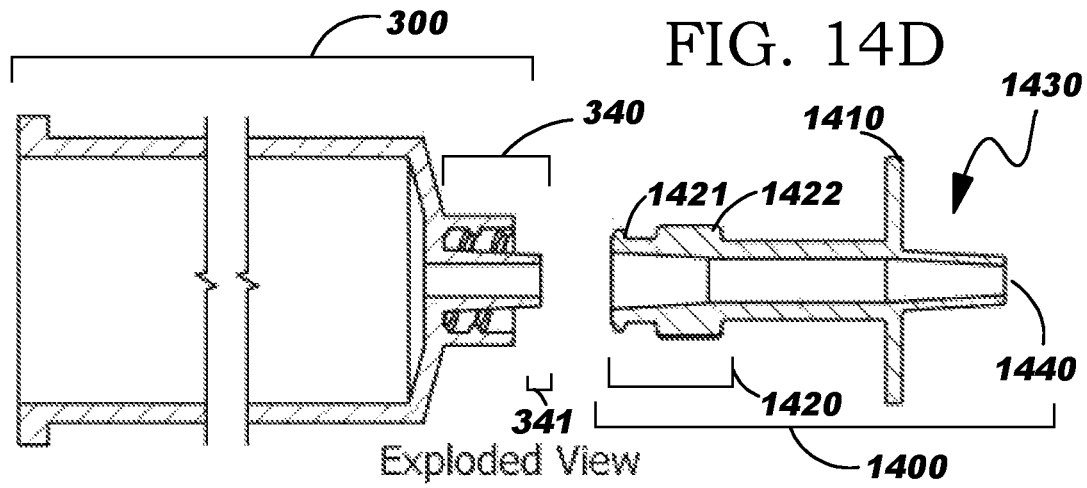

The tips 240, 340 may be generally on the order of ⅜ to 7/16 inch in diameter and generally of similar height (and similarly, tip 140), and are generally constructed of metal. An interior area of this tip is intended for securably attaching a needle and is generally threaded for at least a portion thereof. A height of this threaded area is believed to be generally on the order of ⅛ inch to ¼ inch (and it is believed that a height of 5.4 millimeters, or approximately 0.2125 inches, is used for syringe tip threads that conform to ISO 80369-7:2016). While not illustrated in detail on tips 240, 340 of FIGS. 2 and 3, the syringe tip also typically includes a protrusion (illustrated herein in FIG. 14D; see reference number 341) that is centered within the exterior wall of the tip and that provides the opening through which a substance enters into the syringe barrel. (Notably, tips 140, 240, 340 are not designed for inserting through the rubber membrane of a medicine bottle.)

Syringes 200, 300 are often constructed, at least in part, of metal. Glass or plastic might be used for the syringe barrel. A metal commonly used for syringes, by way of example, is stainless steel; another example is aluminum.

Figure 4:
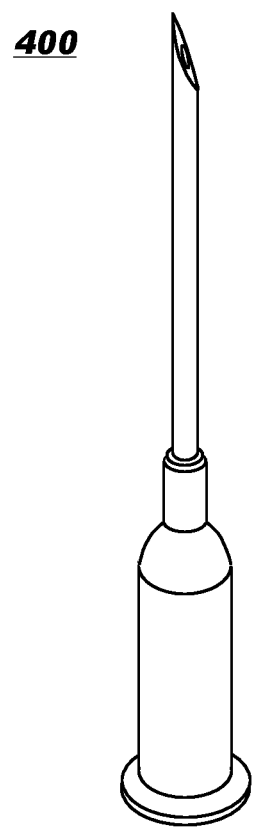
FIG. 4 depicts an example of a prior art needle.
Figure 4A:
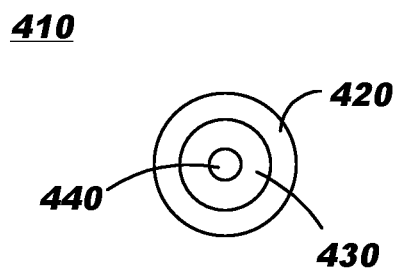
FIGS. 4A and 4B illustrate bottom views showing how a proximal end of a needle may be configured for securable attachment to a syringe.
Figure 4B:
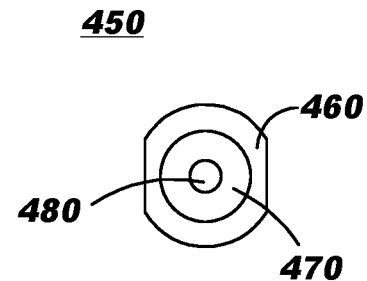

FIG. 4 illustrates an example of a prior art needle 400, which may be affixed to the distal end of syringes 100, 200, or 300. Needles are typically sold in standardized sizes, and thus the distal syringe ends 140, 240, 340 typically conform to the standard size of the proximal end of a needle. FIGS. 4A and 4B illustrate bottom views showing examples of how a proximal end of needle 400 may be configured for securable attachment to the distal end of a syringe that has an internal threaded portion. In an approach 410 as shown in FIG. 4A, a flanged area 420 extends radially outward from the proximal end of the needle (as is generally illustrated in FIG. 4). Reference number 440 depicts the opening in the tip of the needle, and reference number 430 generally depicts the sidewall of needle 400. In another approach 450 as shown in FIG. 4B, a flanged area 460 extends perpendicularly outward from the proximal end of the needle, but in this configuration, is fashioned as having side edges that are not generally round. (Note that it is believed that the flanged area 460 of a needle extends perpendicularly, although more generally, this will be understood as a "lateral" extension. Accordingly, references herein to a "perpendicular" extension for connecting to a syringe should be interpreted more generally as a "lateral" extension for making such connection.) Reference number 480 depicts the opening in the tip of the needle, and reference number 470 generally depicts the sidewall of needle 400. In either case, a flanged area 420, 460 on the proximal end of a needle is designed to securably attach to a corresponding receiving area on the distal end of a syringe. In yet another approach (not illustrated), the securable attachment of a needle to a syringe tip relies on friction instead of an exterior flanged area, whereby the proximal end of needle 400 is placed over an exterior of the distal end (e.g., tip 140 of FIG. 1) of a syringe. These approaches are commonly referred to as a Luer-style lock approach and a Luer-style slip approach, respectively, as is discussed in further detail below. (As is readily understood, a Luer-style lock relies upon a threaded attachment of what are commonly denoted as "male" and "female" parts, which may be achieved by placing tabs as lateral extensions on one part, these tabs designed to rotatably descend within corresponding threads of the other part.) Note that if flanged area 420 is configured to extend perpendicularly outward as illustrated in FIG. 4A, it is preferably intended for use in a Luer-type slip connection rather than a Luer-type lock connection, due to the so-called "double start" or double helix configuration that is described for the internal threads of a Luer-type lock hub according to International Standards 594-1:1986 and 594-2:1998(E) and their replacement ISO 80369-7:2016, which are discussed in further detail below. As an alternative, tabs may be added to the outer edge of flanged area 420, where these tabs are configured for engaging the internal threads of the Luer-type lock hub (and specifications pertaining to such tabs are provided in ISO 80369-7:2016).

For withdrawing fluid medication from a bottle into the barrel of syringe 100, 200, or 300 using known techniques, the sharp tip at the distal end of the needle 400 is inserted through the rubber membrane of the bottle. For subsequently administering the fluid medication from the barrel of the syringe, the sharp tip of that same needle is inserted into an animal's body, and the person holds tab-shaped member 150 while simultaneously depressing plunger 120 of syringe 100, squeezes the handles 210 of pistol-grip syringe 200, or holds tabbed member 350 while simultaneously depressing handle-style tabbed member 320 of tab-handled syringe 300.

This known approach of withdrawing fluid medication from a bottle using a needle and then administering the medication using the same needle works well for fluids having a low viscosity. (Consider, by way of reference, the relative ease of drawing a low-viscosity fluid such as water through the tip/opening of a needle 400 affixed to a syringe.) However, animal medications are marketed that have a relatively high viscosity (that is, they are relatively thick in consistency), and this higher viscosity makes the medications very difficult to withdraw from a bottle using a needle, and also typically more difficult to expel from the syringe. Stated another way, such higher-viscosity medications are not readily "syringeable".

When a medication is not readily syringeable, it may take a considerable amount of time for the person tasked with withdrawing the medication from the bottle to withdraw even a small amount of medication. When a large amount of such medication must be administered, and/or when the higher-viscosity medication must be administered to multiple animals, the person may experience frustration or even fatigue due to this long withdrawal time. As a result, use of the higher-viscosity medication by animal care-givers may be diminished, which may lead to the medication failing to reach its potential market share. Thinning the medication is undesirable as an answer to improving the syringeability problem, as the effectiveness of the medication could be altered.

In addition to the above-described issues with withdrawing higher-viscosity medication into a syringe, the higher viscosity of the medication makes the injection process more time-consuming and physically more difficult for the person tasked with medicating the animal. In particular, the general configuration of a plastic syringe as illustrated in FIG. 1 does not enable a person using the syringe to have sufficient leverage when attempting to inject the medication into an animal. Tab-shaped member 150 is known to collapse or break in some instances, due to the physical force that must be exerted while depressing plunger 120. The plunger shaft is also known to break in some instances, for example due to misalignment as it moves within the barrel or due to age-related brittleness. The needle may also be forced off the syringe when attached thereto by a friction-based Luer-type slip connection, which may in turn lead to leakage and/or waste of the medication through the now-opened end of the syringe. Additionally, the syringe tips of plastic syringes are known to break off while medicating an animal (for example, due to the animal moving or thrashing about), which can lead to waste of medication in the syringe. These problems are more likely to occur with the increased physical force required for injecting higher-viscosity medications.

In sharp contrast to use of a plastic syringe, the syringes 200, 300 of FIGS. 2-3 are better adapted for withstanding the physical force required for expelling a higher-viscosity medication from the syringe barrel and for allowing the person using the syringe to have better leverage during the injection process. (Because the leverage is improved, the time required to complete the injection may be shortened as compared to use of a plastic syringe configured as shown at 100 of FIG. 1, which benefits the person and the animal.)

In view of the above-described issues, preferred embodiments of the present invention are directed toward improved syringeability of medications having a relatively high viscosity. (The disclosed syringe adapter may function suitably with lower-viscosity medications as well, and is therefore not deemed to be limited to use with particular medications.)

A preferred embodiment of the present invention provides a new tip that operates as a syringe adapter for withdrawing medication from a bottle. This tip is preferably affixed to a pistol-grip syringe of the type illustrated in FIG. 2 or a tab-handled syringe of the type illustrated in FIG. 3. The pistol-grip or tab-handled syringe may be formed from plastic, metal, or other substance(s), as noted earlier. Accordingly, use of an embodiment of the present invention addresses the issue of drawing a higher-viscosity fluid from a bottle as well as the issue of providing sufficient leverage for subsequent injection. That is, the larger opening of the disclosed syringe adapter (as compared to a conventional needle) addresses syringeability issues by improving draw time of higher-viscosity medications and, when this adapter is affixed to a pistol-grip or tab-handled syringe, the medication withdrawn into the pistol-grip or tab-handled syringe can be more easily administered from the syringe barrel (noting that, in some embodiments, the syringe adapter will be replaced with a needle prior to injecting the medication).

While discussions herein refer to preferably using the disclosed syringe adapter with a pistol-grip or tab-handled syringe, it should be noted that the disclosed syringe adapter may also be used advantageously with a syringe of the type shown in FIG. 1 (and such usage is within the scope of the present invention).

Figure 5:
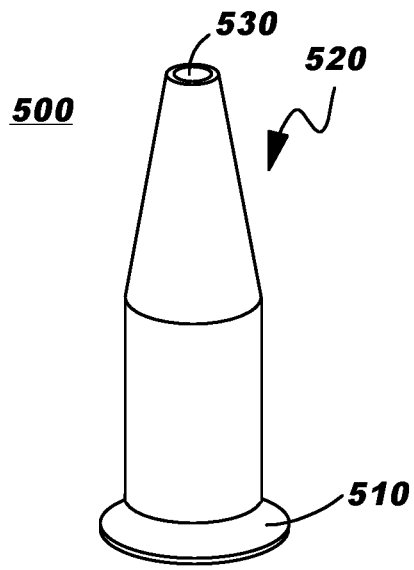
FIGS. 5-6 illustrate first and second preferred embodiments of the syringe adapter disclosed herein.

FIG. 5 illustrates one embodiment of the syringe adapter disclosed herein. The syringe adapter has a sidewall extending between a proximal end (i.e., the end on which reference number 510 is located) and a distal end (denoted generally at 520), and the interior surface of the sidewall defines a chamber through which fluid medication flows. The length and shape of the syringe adapter, as well as the thickness of portions of the sidewall and the width of its interior chamber, may vary from illustrations depicted herein without deviating from the scope of the present invention. In the embodiment illustrated in FIG. 5, the shape of the syringe adapter 500 is generally conical in an upper portion and generally cylindrical in a lower portion. While not illustrated in FIG. 5, an interior of at least a portion of the lower portion is preferably tapered, with a 6 percent taper extending from the proximal end toward the distal end. This tapered shape conforms the interior surface to the above-noted International Standards ISO 594-1:1986 and ISO 594-2:1998(E) and their replacement ISO 80369-7:2016, which are directed toward conical fittings for health-care applications. Preferably, the overall length of the syringe adapter is not shorter than ⅜ to ½ inch, by way of illustration but not of limitation, as this length will enable the syringe adapter to sufficiently extend into a bottle of medication to be withdrawn. An upper range of the overall length, conversely, may be on the order of 1 to 2 inches, by way of illustration but not of limitation.

A preferred diameter of the hole in the distal end of the tip of the syringe adapter is on the order of 0.10 inches, although embodiments are not limited to this diameter (as discussed in further detail hereinafter). Thickness of the sidewall of the syringe adapter is preferably on the order of 0.05 inches, although embodiments are not limited to this thickness. Using a sidewall thickness of 0.05 inches and an opening of 0.10 inches results in a syringe adapter having an overall diameter of 0.20 inches at the end to be inserted into the bottle of medication, in this example configuration. Advantageously, it is noted that the opening formed by the sidewall at the distal end of an embodiment of the syringe adapter is depicted herein as generally blunt, as contrasted with a sharp metal point found on the tip of a needle, thereby improving safety for someone who may, for example, carry a syringe adapter on his or her person.

Preferably, the proximal end of the disclosed syringe adapter attaches to a syringe using a Luer-type lock or a Luer-type slip (although it will be understood that this is by way of illustration and not of limitation). Luer-type locks and Luer-type slips are known approaches for making leak-free connections on fluid fittings, and are described in the above-cited International Standards. A Luer-type lock provides a threaded attachment, whereby two pieces of a configuration are held together by rotating a flanged area (such as flanged area 460 of FIG. 4B) of one piece within threads of the other piece, whereas a Luer-type slip is non-threaded and provides attachment using friction. In one approach for securably attaching syringe adapter 500 using a Luer-type lock, the syringe adapter 500 as illustrated in FIG. 5 has an external flanged area 510 on the proximal end (shown without tabs extending from the outer edge, for drafting convenience), and a two-part connection is made by inserting this flanged end into corresponding internal threads on a distal end of a syringe (as discussed above with reference to the syringe tips illustrated at 240, 340). As noted earlier, a conventional height for this internal threaded portion of a pistol-grip or tab-handled syringe tip is believed to be approximately ⅛ inch to ¼ inch in length and a standardized height thereof is believed to be 5.4 millimeters, and accordingly, a flanged area 510 on the proximal end of syringe adapter 500 is preferably on the order of at least 1/16 to ⅛ inch in height. The shape of flanged area 510 may correspond generally to flanged area 420 or 460 (for example, by extending radially or perpendicularly from the proximal end of the syringe adapter, although a strictly circular shape is not required), although another shape providing for a securable attachment may be used without deviating from the scope of the present invention. (In view of this ability to use shapes other than strictly circular for securable attachment, it will be readily understood that references herein to "radial" or "radially" may be more generally understood as "lateral" or "laterally".) Notably, with regard to the securable attachments noted herein that are described as preferably using a Luer-lock connection, it will be readily understood that the shape and size of the attachment area—such as the area denoted in FIG. 5 by reference number 510—preferably conforms to the well-known shape and size required for such connection.

In another approach, the proximal end of the syringe adapter 500 may omit the flanged area shown at 510 and is attached and held to the distal end of the syringe by friction in a Luer-type slip approach. It will be noted that reference number 530 denotes the location of the opening in the distal end of syringe adapter 500.

Figure 6:
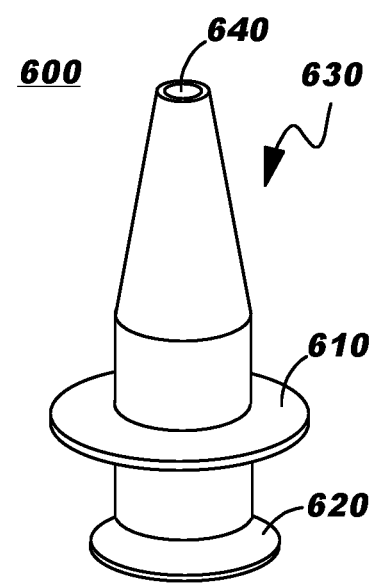

FIG. 6 illustrates another embodiment of the syringe adapter disclosed herein. In this embodiment, syringe adapter 600 includes a radial extension feature 610, which is preferably configured as extending perpendicularly and radially outward from the body of the syringe adapter and is shown in FIG. 6 as being located relatively near to the proximal end of syringe adapter 600 (where the proximal end of syringe adapter is the end on which reference number 620 is located, and the distal end is denoted generally by reference number 630; reference number 640 denotes the location of the opening in this distal end)). (Alternatively, radial extension feature 610 may be placed at another location on the syringe adapter, for example being located closer to the conical portion thereof) In addition to enabling a person to more easily grasp the syringe adapter 600, the radial extension feature 610 also serves to prevent inserting the syringe into the medication bottle far enough that the attachment point (e.g., Luer-type slip or lock) between the syringe and the syringe adapter would come into contact with the medication. Stated another way, an extension feature (or equivalently, "extension member") is preferably sized so as to halt insertion of the syringe adapter into the container beyond a location of the extension feature. Accordingly, in a preferred embodiment, a diameter of radial extension feature 610 is sufficiently large as to meet or exceed the diameter of a conventional rubber membrane on a medicine bottle, although it will be understood that embodiments are not limited to this diameter. The diameter of radial extension feature 610 may be, by way of example, on the order of twice the diameter of the cylindrical portion of syringe adapter 600. (Syringe adapter 600 may omit the flanged area 620 when relying on a Luer-type slip attachment, and is depicted without tabs extending from the outer edge for drafting convenience, as was discussed above with reference to flanged area 510.)

An extension feature might alternatively be used that is not round, although this has not been illustrated in FIG. 6. (In view of this ability to use an extension feature that is not round, it will be readily understood that references herein to a "radial" extension feature are by way of illustration but not of limitation and are not to be construed as requiring the extension feature to have a round outer edge. More generally, the extension feature may be termed a "lateral" extension feature or simply as an "extension feature".) As noted above, a preferred diameter for the extension feature (as illustrated by the example at reference number 610) is selected to provide compatibility with a size of the rubber membrane on a bottle from which fluid will be withdrawn. It will be readily understood that a common diameter of the rubber membrane fitted in the top of bottles holding 250 milliliters ("ml") of fluid and also bottles holding 500 ml is 0.75 inches. (Most common multi-dose fluid medication bottles are sold in bottles having volumes of 100 ml, 250 ml, and 500 ml, while some less-common smaller-dose bottles hold 20 ml of fluid.) It is readily understood that a common outer diameter of the top of such bottles is about 1.3 inches. Accordingly, a preferred diameter for the extension feature when used with such bottles is in the range of about 0.50 inches to about 1.3 inches, and more preferably, the diameter is about 0.70 inches to about 0.80 inches, and most preferably, is about 0.75 inches as noted herein. The range in size for the extension feature has been selected, through experimentation and testing, by noting that an extension diameter appreciably exceeding the outer width of the medicine bottle may be cumbersome for the person holding the bottle and the syringe with affixed syringe adapter, and that an extension feature diameter about the diameter of the rubber membrane—or ranging between about the diameter of the rubber membrane and about the outer diameter of the top of the bottle—provides an advantageous size that allows the person to grip the outer edges of the extension feature while also gripping the bottle, and at the same time, also ensuring that the extension feature is unlikely to push through the rubber membrane. If used with a bottle having other dimensions than those noted above, it will be understood that the diameter of the extension feature may be adapted to provide compatibility therewith. In such adaptation, it is preferred that the diameter of the extension feature is preferably within about the diameter of the rubber membrane and about the outer diameter of the top of the bottle, and more generally, ranges between about two-thirds the diameter of the rubber membrane and about the diameter of the top.

A preferred material for the disclosed syringe adapter is plastic, which will allow it to be economically produced as a disposable item, although another material may be used without deviating from the scope of the present invention. As one alternative to use of plastic, the syringe adapter or portion(s) thereof may be constructed from stainless steel, aluminum, or another metal (or combinations thereof), noting that metal generally provides increased strength and durability as compared to plastic. It will be readily understood that constructing the syringe tip adapter from a material such as plastic advantageously allows it to be recyclable, in addition to being easily disposable (as contrasted to disposal of a sharp needle, for which care must be taken upon disposal to ensure that, inter alia, persons or animals are protected from injury therefrom). Notably, the disclosed syringe adapter does not need to come into physical contact with a particular animal (i.e., because the physical contact occurs at the needle used to inject the medication), and thus re-use of the syringe adapter for medicating multiple animals need not introduce cross-contamination concerns.

Figure 7:
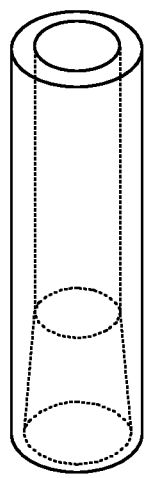
FIGS. 7-8 illustrate alternative embodiments of the syringe adapter disclosed herein.
Figure 8:
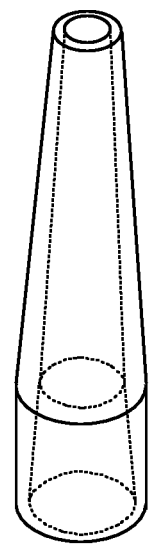

While FIGS. 5 and 6 illustrate a syringe adapter shape that is generally conical in an upper portion and generally cylindrical in a lower portion, this is by way of illustration and not of limitation. As one alternative embodiment, an outer shape of the syringe adapter may be generally cylindrical while preferably having a tapered interior shape for at least a portion of the proximal end, noting that such interior taper enables the syringe adapter to comply with the above-cited International Standards. This alternative embodiment is illustrated in FIG. 7, where dotted lines are used to illustrate a general shape of the interior. FIG. 8 provides another alternative embodiment, where an outer shape of the syringe adapter may be generally conical in an upper portion and generally cylindrical in a lower portion, and in this alternative, the relative length of the upper and lower portions varies from the embodiments illustrated in FIGS. 5 and 6 (and again, at least a portion of such configuration preferably has a tapered interior shape at the proximal end, as shown by the dotted lines, to thereby conform to the above-cited International Standards). Notably, as compared to the cylindrical exterior shape as illustrated in FIG. 7, the exterior taper of the upper portion as illustrated in FIGS. 5-6 and 8 may tend to provide a better seal, and thus be less likely to leak, during such time as the syringe adapter is inserted through the rubber membrane of a bottle. While not illustrated in FIG. 7 or 8, a radial extension member (such as that shown at reference number 610 of FIG. 6) may be added to these configurations if desired.

Figure 9:
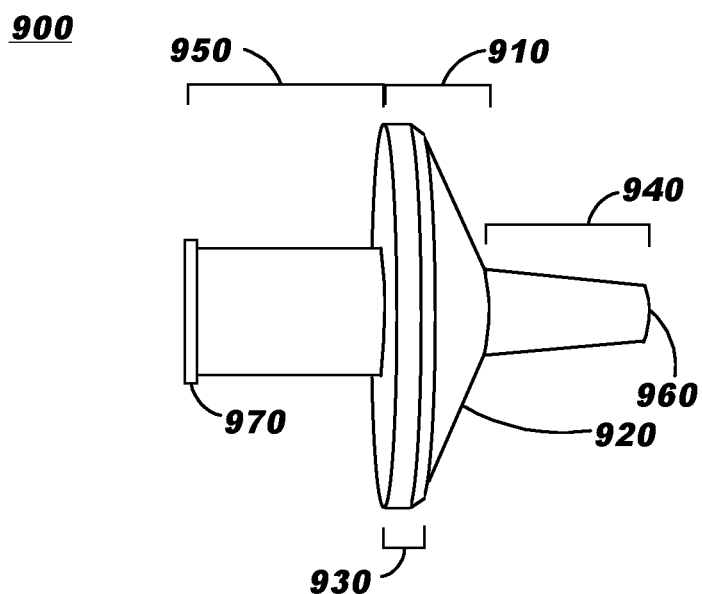
FIG. 9 illustrates a still further embodiment of the syringe adapter disclosed herein.

FIG. 9 illustrates yet another embodiment of the disclosed syringe adapter. In this embodiment, syringe adapter 900 includes a radial extension feature 910, similar to the previously-discussed radial extension feature 610 of FIG. 6. FIG. 9 depicts radial extension feature 910 as being located approximately midway along the length of the syringe adapter, by way of illustration but not of limitation. Whereas the radial extension feature illustrated at 610 of FIG. 6 is illustrated as having a disk-like shape with generally flat upper and lower surfaces, FIG. 9 illustrates an alternative shape where an upper surface of the radial extension feature 910 has a somewhat domed or tapered shape. This tapered or domed portion is shown at reference number 920 and sits atop a disk-like portion 930. Optionally, the lower surface of the radial extension feature may taper in addition to, or instead of, the upper surface thereof, although this has not been illustrated. (Note that the particular shape and dimensions of portions 920, 930 may vary, and thus FIG. 9 provides one example by way of illustration but not of limitation.)

FIG. 9 also illustrates the upper portion 940, at the distal end, of the syringe adapter 900 as having a generally conical shape which is somewhat less tapered than the upper portion as illustrated for the syringe adapters 500, 600 of FIGS. 5 and 6, and having a generally cylindrical shape for the lower portion 950, located at the proximal end of syringe adapter 900. Reference number 960 denotes the location of the opening in the distal end of syringe adapter 900. (As noted below with regard to FIG. 10, the proximal end of the syringe adapter preferably makes a Luer-type lock connection with the tip of a syringe, and it will therefore be readily understood that the shape illustrated at 970 is merely an example and is not to be construed as limiting.)

By way of illustration but not of limitation, a length of the conical portion 940 may be 0.32 inches; a length of the cylindrical portion 950 may be 0.48 inches; a height or thickness of portion 930 may be 0.07 inches; a diameter of radial extension feature 910 may be 0.75 inches; a diameter of the distal and proximal ends of conical portion 940 may be 0.156 inches and 0.174 inches, respectively; and a diameter of cylindrical portion 950 may be 0.24 inches. (When using the above-noted preferred sidewall thickness of 0.05 inches, and if the thickness is uniform throughout, it will be noted that these illustrative measurements indicate an example where the inner diameter of the cylindrical portion 950 is 0.14 inches and the inner diameter of the distal and proximal ends of conical portion 940 are 0.056 inches and 0.074 inches, respectively.)

Figure 10:
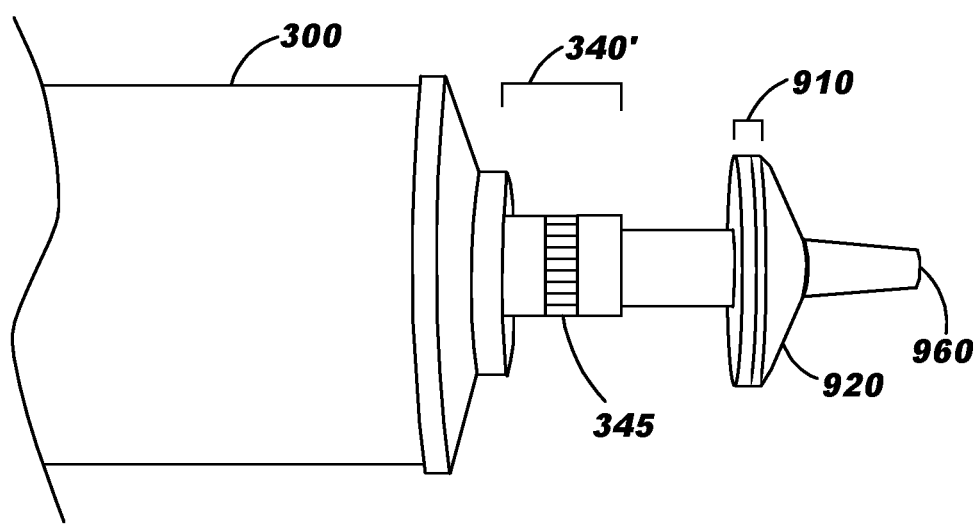
FIG. 10 illustrates a syringe adapter placed upon a syringe.

FIG. 10 illustrates placement of a syringe adapter on a syringe. By way of illustration but not of limitation, the syringe in FIG. 10 corresponds to the tab-handled syringe 300 of FIG. 3 and the syringe adapter corresponds to the embodiment shown at 900 of FIG. 9. Syringe tip 340' provides a point of attachment for the syringe adapter 900, and syringe tip 340' is shown as being generally cylindrical; as contrasted with syringe tip 340 as earlier illustrated, syringe tip 340' is shown with a ribbed exterior mid-section 345 that may provide for a person to securely grip the syringe tip 340' while the syringe adapter 900 is being inserted therein (or removed therefrom). The connection between syringe tip 340' and syringe adapter 900 is preferably a Luer-type lock, but a Luer-type slip may be used alternatively without deviating from the scope of the present invention. (It will be understood that in FIG. 10, a portion of the proximal end of syringe adapter 900 is located inside the distal end of tip 340', following the connection.)

Figure 11:
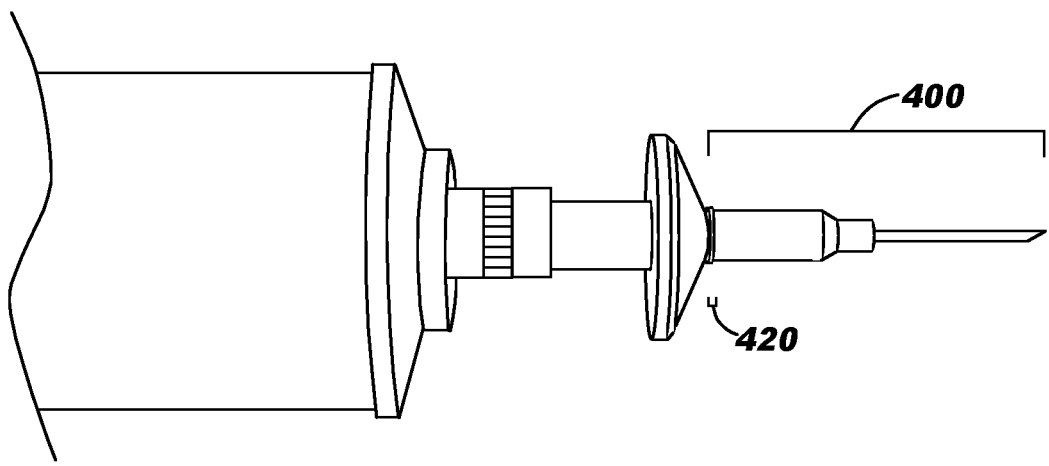
FIG. 11 illustrates a needle placed upon a syringe adapter.

FIG. 11 illustrates one example of placement of a needle on a syringe adapter, for an embodiment in which the syringe adapter remains in place while medication is administered through an attached needle. By way of illustration but not of limitation, the syringe adapter in FIG. 11 corresponds to the embodiment shown at 900 of FIG. 9, the attachment between the syringe and syringe adapter 900 corresponds to the attachment illustrated in FIG. 10, and the needle corresponds to the needle 400 of FIG. 4. In FIG. 11, needle 400 is shown as having its proximal end placed over the distal end of the syringe adapter. In this example, needle 400 includes a small flanged area 420 that enables it to securably attach to the interior of a Luer-type lock, although the illustrated attachment in FIG. 11 is a Luer-type slip connection. Accordingly, the needle 400 may be attached to, and removed from, the syringe adapter with relative ease (e.g., by pushing the proximal end of the needle onto the distal end of the syringe adapter and pulling it therefrom, respectively).

Note that while flanged area 420 is shown as directly abutting the portion of the syringe adapter shown as having a domed shape, this is by way of illustration: alternatively, there may be a gap beneath flanged area 420.

Figure 12:
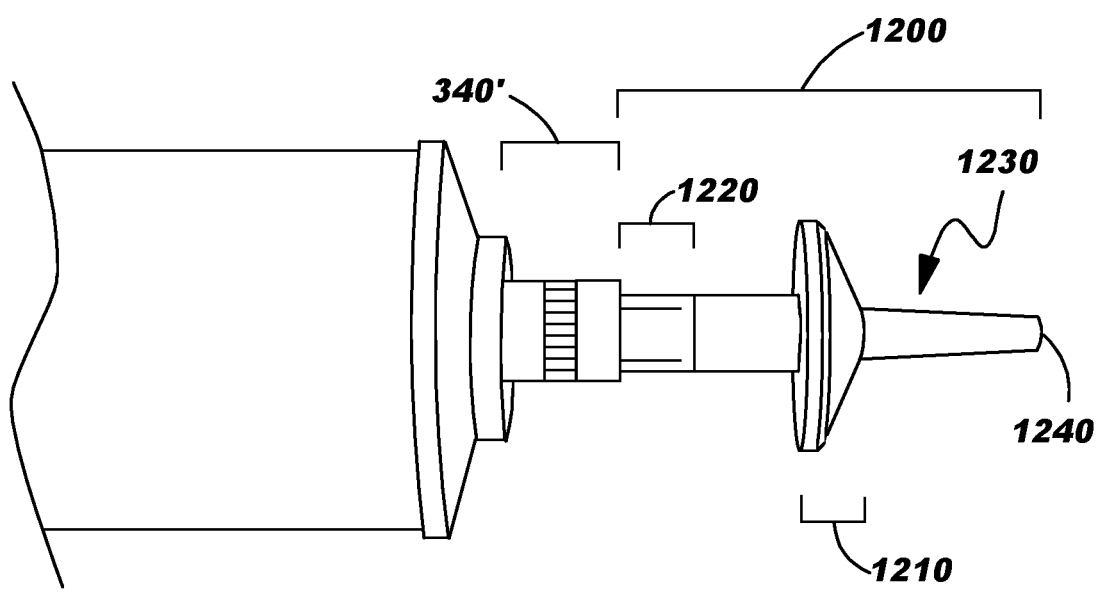
FIGS. 12 and 13 illustrate yet other embodiments of the syringe adapter disclosed herein, and also illustrate placement thereof upon a syringe.

FIG. 12 illustrates still another embodiment of the disclosed syringe adapter, and its placement on a syringe. In this embodiment, syringe adapter 1200 includes a radial extension feature 1210 with a tapered or domed upper surface, similar to the previously-discussed radial extension feature 910 of FIG. 9. As contrasted to syringe adapter 900, the conical portion of the syringe adapter 1200 is somewhat longer (and it should be noted that embodiments of the present invention are not limited to a specific dimension, as has been discussed).

FIG. 12 also illustrates a Luer-type connecting member 1220 affixed to the proximal end of syringe adapter 1200 (where 2 horizontally-oriented "ribs" are illustrated on an upper portion of the surface of member 1220, by way of illustration but not of limitation, and may serve as a grasping member that assists a person using the connecting member in firmly grasping). This connecting member 1220 is shown in FIG. 12 as connecting syringe adapter 1200 to a syringe, which may be syringe 300 of FIG. 3 (by way of illustration but not of limitation). The point of connection on syringe 300 is shown in FIG. 12 as comprising a syringe tip 340', similar to that which was discussed above with reference to FIG. 10 by way of illustration, into which the proximal end of connecting member 1220 of syringe adapter 1200 is removably inserted. In one approach, connecting member 1220 is made from metal while remaining portions of syringe adapter 1200 are made from plastic, and a bond is made between the metal and plastic during manufacturing. Preferably, connecting member 1220 attaches to syringe tip 340' with a Luer-type lock connection (rather than a Luer-type slip connection). While not shown in FIG. 12, connecting member 1220 preferably includes a flanged area at its proximal end (such as flanged area 460 of FIG. 4B), and the Luer-type lock connection is made by inserting this flanged area of connecting member 1220 into syringe tip 340' and then twisting the syringe adapter 1200 until the flanged area locks into place in the internal threaded portion of the syringe tip 340'. This type of connection is deemed beneficial for providing a more secure attachment between the syringe and the syringe adapter. Reference number 1220 generally denotes the proximal end of syringe adapter 1200, although as stated above, a portion of the proximal end is located within syringe tip 340' and is therefore not shown. Reference number 1230 generally denotes the distal end of syringe adapter 1200, while reference number 1240 denotes the location of the opening therein.

Figure 13:
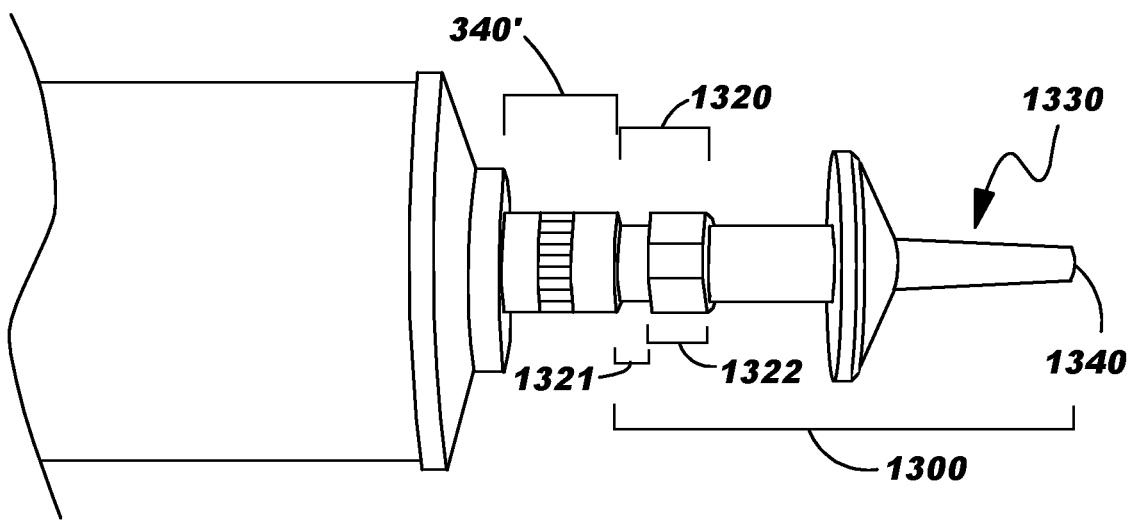

FIG. 13 illustrates yet another embodiment of the disclosed syringe adapter and its placement on a syringe. In this embodiment, syringe adapter 1300 differs from syringe adapter 1200 of FIG. 12 in that a Luer-type connecting member 1320 affixed to the proximal end of syringe adapter 1300 uses a different configuration. As shown in FIG. 13, an upper portion 1322 of connecting member 1320 has a multi-sided exterior shape, shown by way of illustration as being hexagonal in at least a portion thereof, which may serve as a grasping member that assists a person using the syringe adapter in firmly grasping. More particularly, in the example shown in FIG. 13, connecting member 1320 has a hexagonal upper portion 1322 and a cylindrical lower portion 1321. In one approach, connecting member 1320 is made from metal while remaining portions of syringe adapter 1300 are made from plastic, and a bond is made between the metal and plastic during manufacturing. Preferably, connecting member 1320 attaches to syringe tip 340' with a Luer-type lock connection (rather than a Luer-type slip connection). While not shown in FIG. 13, connecting member 1320 preferably includes a flanged area at its proximal end (such as flanged area 460 of FIG. 4B), and the Luer-type lock connection is made by inserting this flanged area of connecting member 1320 into syringe tip 340' and then twisting the syringe adapter 1300 until the flanged area locks into place in the internal threaded portion of the syringe tip 340'. As noted above, the Luer-type lock connection is deemed beneficial for providing a more secure attachment between the syringe and the syringe adapter. Reference number 1320 generally denotes the proximal end of syringe adapter 1300, although as stated above, a portion of the proximal end is located within syringe tip 340' and is therefore not shown. Reference number 1330 generally denotes the distal end of syringe adapter 1300, while reference number 1340 denotes the location of the opening therein.

FIG. 14 (comprising FIGS. 14A through 14D) illustrates a further embodiment of the disclosed syringe adapter, showing exterior views as well as cross-sectional views of placement thereof upon a syringe and as exploded. By way of illustration but not of limitation, the syringe in FIG. 14 corresponds to the tab-handled syringe 300 of FIG. 3 with its syringe tip 340. Syringe adapter 1400, in this embodiment, includes a radial extension member 1410 and the proximal end as denoted by reference number 1420 includes a Luer-type connecting member, where proximal end 1420 in turn includes a flanged area 1421 at its proximal end (such as flanged area 460 of FIG. 4B) for removably attaching syringe adapter 1400 to the distal end of syringe 300 and an upper portion 1422. The Luer-type lock connection is made by inserting flanged area 1421 of proximal end 1420 into syringe tip 340 and then twisting the syringe adapter 1400 until the flanged area 1421 locks into place in the internal threaded portion of the syringe tip 340 (as illustrated in the non-exploded cross-sectional view of FIG. 14C) to thereby provide a secure attachment between the syringe and the syringe adapter. As noted above with reference to the ribs at 1220 and upper portion 1322, upper portion 1422 may serve as a grasping member that assists a person using the syringe adapter with firmly grasping (for example, while inserting and twisting the flanged area 1421 into the syringe tip 340). Reference number 1430 generally denotes the distal end of syringe adapter 1400, while reference number 1440 denotes the location of the opening therein. (As can be seen with reference to FIGS. 14C and 14D, embodiments are not limited to using a uniform sidewall thickness throughout.)

Use of the disclosed syringe adapter while medicating an animal operates, in some embodiments, as follows: the syringe adapter is affixed to a syringe (which, as noted earlier, is preferably a pistol-grip or tab-handled syringe); the syringe adapter is inserted into a bottle of medication; the plunger of the syringe is pulled back to withdraw the desired dosage of medication from the bottle into the syringe barrel; the syringe adapter is removed from the bottle, while the plunger remains stationary; the syringe adapter is replaced with a needle; and the medication (or some portion thereof) is then injected by pushing the plunger forward (for example, by squeezing the pistol-grip handles or pressing down on the tabbed handle) to expel medication from the syringe barrel. If it is desired to reuse the syringe adapter, then the needle is removed from the syringe, after which the above process is repeated. (As noted earlier, the disclosed syringe adapter is not limited to use with medication intended for any particular type of animal life, and therefore the medication may be injected more generally into a "target" or a "recipient".)

Use of the disclosed syringe adapter operates, in some other embodiments, as follows: the syringe adapter is affixed to a syringe (preferably a pistol-grip or tab-handled syringe); the syringe adapter is inserted into a bottle of medication; the plunger of the syringe is pulled back to withdraw the desired dosage of medication from the bottle into the syringe barrel; the syringe adapter (which remains attached to the syringe) is removed from the bottle, while the plunger remains stationary; a needle is affixed to the syringe adapter (and note that the syringe adapter remains affixed to the syringe); and the medication (or some portion thereof) is then injected by pushing the plunger forward (for example, by squeezing the pistol-grip handles or pressing down on the tabbed handle) to expel medication from the syringe barrel. If it is desired to reuse the syringe adapter (for example, for withdrawing additional fluid for medicating another animal), then the needle is removed from the syringe adapter, after which the above process of withdrawing medication using the syringe adapter, affixing a needle thereto, and then injecting the medication (or some portion thereof) is repeated.

It should be noted that while preferred embodiments are described herein as conforming to the above-cited International Standards and/or as using Luer-type connections to a syringe, this is by way of illustration but not of limitation. It should also be noted that the figures are directed toward illustrating aspects of the present invention, in combination with descriptions herein, and aspects shown therein (for example, length, width, and/or taper) are not necessarily drawn to scale. It should also be noted that while discussions herein refer primarily to making a locking connection by twisting a first feature within a second feature, it will be obvious that the second feature may be twisted within the first feature or that both features may be twisted, without deviating from the scope of the present invention.

While medications have been discussed herein as commonly being sold in a multi-dose bottle, this is by way of illustration and not of limitation. The disclosed syringe adapter may be used beneficially for medication that is sold in a single-use dosage. Also, it should be noted that while some discussions herein refer to expelling "the withdrawn medication" or "emptying" the syringe, this is by way of illustration and not of limitation: the scope of the present invention does not require withdrawn medication to be expelled in full nor does it require a syringe to be fully emptied.

Advantageously, the disclosed syringe adapter may be included with purchase (e.g., within the packaging) of a higher-viscosity medication. As one alternative, a multi-pack of the disclosed syringe adapter may be included with such purchase, particularly when the medication is sold in a multi-dose bottle. The disclosed syringe adapter may also be sold separately from medication. Advantageously, a supplier of packaged syringe adapters may ensure that they are sterilized and/or sanitized by distributing them in sealed packaging.

Examples of higher-viscosity animal medications with which the disclosed syringe adapter may be used beneficially include Nuflor®, Nuflor Gold®, and Resflor Gold®. ("Nuflor", "Nuflor Gold", and "Resflor Gold" are registered trademarks of Intervet Inc. in the United States, other countries, or both. Intervet is now known as "Merck Animal Health".) These medications are commonly sold in 500-milliliter multi-dose bottles and may be administered, by way of example, in dosages of 36 to 60 milliliters per animal. Accordingly, a single multi-dose bottle may be used to treat generally 8 to 14 animals at this dosage range.

As noted earlier, viscosity of a substance may vary with temperature. Viscosity is commonly measured in units termed "centipoise", which may be abbreviated as "cP" or "cps". Water, at 70 degrees Fahrenheit, has a viscosity of approximately 1 cps, and by way of comparison, blood generally has a viscosity of about 10 cps. By convention, a temperature of 70 degrees Fahrenheit is used as a reference point for measuring cps, and thus when a temperature is not mentioned for a particular cps measurement, it should be assumed that the temperature associated with the stated measurement is 70 degrees Fahrenheit.

According to a study documented in "Syringeability and Viscosity Comparative of Different Florfenicol Formulations" by S. Colomer, et al., date unknown, the viscosity of Nuflor® at 5 degrees Celsius (which is approximately 41 degrees Fahrenheit) was 321 cps. U.S. Pat. No. 8,034,845, titled "Compositions and Method for Treating Infection in Cattle and Swine", discusses a formulation believed to correspond to Nuflor Gold® and states that formulations of the invention disclosed therein preferably "have a viscosity of less than about 125 cps".

An embodiment of the present invention is believed to be advantageous for fluid medications having a viscosity of at least 50 to 100 cps at a temperature of at least 5 degrees Celsius, as well as for fluid medications having a higher cps at this temperature (noting, as stated above, that viscosity varies with temperature).

FIG. 15 presents tables containing measurements from tests conducted to compare use of a sample version of the disclosed syringe adapter to use of conventional needles. The tested medication was Resflor Gold®, and a withdrawn quantity thereof was 30 cc (computed as a desired volume for treating an animal with a body weight of 500 pounds). Results of these tests will now be discussed.

In a first test (denoted "Test #1" in FIG. 15), the medication was at room temperature. A withdrawal rate was measured using an 18-gauge needle having a 1-inch length, a 16-gauge needle having a ⅝-inch length, and the syringe adapter. A 16-gauge needle has a larger tip opening than an 18-gauge needle, and will therefore withdraw a solution faster than the 18-gauge, although the 16-gauge needle is thought to be disfavored for at least some situations because it may allow the (relatively expensive) medication to leak out of the animal during the medicating process. In addition, a 16-gauge needle is thought to be too large to use on smaller animals. In the sample version, the diameter of the opening in the distal end of the syringe adapter was approximately 0.094 inches.

In this first test, the bottle of medication was placed upon a table and the syringe adapter was already mounted upon a syringe held by the tester, and the elapsed withdrawal times include picking up the bottle and inserting the syringe adapter into the bottle. As shown in FIG. 15, withdrawing 30 cc of Resflor Gold® in this test environment required 3 minutes 50.30 seconds using the 18-gauge needle and 35 seconds using the 16-gauge needle, as compared to 8 seconds using the syringe adapter.

Time to expel the 30 cc of medication was also tested in this first test. Expelling the medication in this test environment required 35 seconds using the 18-gauge needle and 11 seconds using the 16-gauge needle. (Time to expel the medication was not measured using the syringe adapter, because the expel time depends on the needle used for injecting the medication.)

In a second test (denoted "Test #2" in FIG. 15), the medication was again at room temperature, but the bottle of medication was now held by the tester to eliminate time required to pick up the bottle. Accordingly, the elapsed withdrawal times in this test begin with inserting the syringe adapter into the bottle. As shown in FIG. 15, withdrawing 30 cc of Resflor Gold® in this test environment required an average of 5.54 seconds when using the syringe adapter, where this average was computed by taking measurements 6 times and discarding a time that appeared to be an outlier. (Because slightly more than 2 seconds were gained by omitting the "pick up" time of the bottle, this test was not performed using the needles: it may be assumed that the withdrawal times using needles in the first test would be approximately 2 seconds less under the environment of this second test.)

In a third test (denoted "Test #3" in FIG. 15), the medication was now at a temperature of approximately 38 to 40 degrees Fahrenheit, having just been removed from refrigeration (noting that this temperature was intended to simulate a cold weather environment in which the tested medication might be used). The bottle of medication and syringe with affixed syringe adapter were again held by the tester (and the elapsed times began with inserting the syringe adapter into the bottle), as in the second test. As shown in FIG. 15, withdrawing 30 cc of the now-cooler-temperature Resflor Gold® in this test environment required 3 minutes 42.27 seconds using the 16-gauge needle, as compared to 1 minute 1 second using the syringe adapter. Note that this third test was not conducted using the smaller 18-gauge needle, but by comparison to the results of the first test, it can be seen that the withdrawal time using the smaller (i.e., 18-gauge) needle may be expected to greatly exceed the nearly 4-minute withdrawal time for the 16-gauge needle.

While a preferred diameter for the hole, or opening, in the distal end of the syringe adapter is about 0.10 inches, embodiments disclosed herein are not limited to this preferred diameter, as noted earlier. Instead, a syringe adapter as disclosed herein may have an opening, or distal end hole, within any suitable range. In addition to the tests discussed above with reference to FIG. 15, which were conducted using a sample version of the syringe adapter in which the distal end opening measured approximately 0.094 inches, additional experiments and testing have been performed using syringe adapter prototypes with a range of sizes for the distal end opening of the syringe adapter, in view of both draw time and impact upon the rubber membrane, and those results will now be discussed.

When considering an upper bound on the size of the opening in the distal end of the syringe adapter, it will be readily understood that throughput time of a fluid drawn into a syringe is necessarily limited by the size of the opening into the syringe itself (that is, the opening at the distal end of the syringe). It is believed that commercially-available syringes adhere to a standardized maximum outer diameter for the tip of a syringe, where this standardized maximum outer diameter is stated in the above-cited International Standards as about 0.1585 inches. These International Standards do not appear to state a standardized inner diameter for the tip of a syringe, and accordingly, the measurement of 0.1585 inches necessarily provides an upper bound on the inner diameter of the syringe tip and therefore on the width of the opening through which fluid will enter the syringe. It is noted that commercially-available syringes have distal end openings in different inner diameters. Several commercially-available syringes were measured, and were found to have distal end openings that range from an inner diameter of 0.0625 inches to 0.1094 inches, for example. In view of this information, it is noted that the draw time when using a syringe adapter will not be appreciably improved by increasing the syringe adapter distal end opening size beyond the limiting size of the opening into the syringe itself. Accordingly, for a syringe having an opening with a maximum inner diameter of about 0.1585 inches, a measurement of about 0.1585 inches forms a de facto upper bound on the size of the distal end opening of the disclosed syringe adapter. In the more general case where the distal end opening of a syringe is smaller, an inner diameter of the distal end opening in the syringe adapter preferably provides compatibility with the size of an inner diameter of the distal end opening into such syringe. Advantageously, using a distal end opening with an inner diameter on the order of the 0.1 inch measurement previously noted herein provides compatibility with a plurality of different syringe opening sizes.

It is noted that a standard opening size for the 16-gauge needle used in the testing of FIG. 15 is about 0.047 inches, and that the above discussion of FIG. 9 referred to an example where the diameter of the distal end of conical portion 940 is approximately 0.156 inches (and when using a sidewall thickness of 0.05 inches, an inner diameter of approximately 0.056 inches). Additional experiments and testing used prototypes with additional opening sizes at the distal end of the syringe adapter to validate earlier conclusions. Draw times using conditions analogous to Test #1 of FIG. 15 were measured for syringe adapter prototypes having distal end inner diameters in increments of 1/64 inch, from decimal measurements of 0.0625 inches through 0.171875 inches (corresponding to 4/64 inches through 11/64 inches), as well as a prototype having a 0.09 inch distal end inner diameter. The average draw time for the prototype with a 0.0625 inch inner diameter was 19.67 seconds. While this is notably improved over the results of the 18-gauge and 16-gauge needles of Test #1, it is significantly less attractive than the average draw time noted for the prototype having the 0.09 inch inner diameter, which had an average draw time of 5.88 seconds. The prototype having a distal end inner diameter of 0.078125 inches yielded an average draw time of 8.45 seconds, showing very significant improvement over the next-smaller 0.0625 inch opening. All remaining prototype sizes in this testing (ranging from 0.09375 inches to 0.17185 inches) showed an average draw time within 0.5 seconds of the prototype with the 0.09 inch inner diameter—notably leveling off in draw time improvement, in spite of increasing the distal end inner diameter, to a variance that will not be detectable by a user. (For example, the average draw times for the prototypes with distal end inner diameters of 0.14 inches and 0.15625 inches were 5.82 seconds and 5.81 seconds, respectively, while the average time for the inner diameter of 0.109 inches was 6.11 seconds.) In view of this information, a preferred inner diameter of the distal end opening in the syringe adapter is in the range of about 0.05 inches to about the maximum size of the distal end opening into the syringe (believed to be about 0.1585 inches, as noted above), and more preferably, this inner diameter is about 0.078 inches to about 0.14 inches, and even more preferably, is about 0.09 inches to about 0.11 inches, and generally, is about 0.10 inches.

A consideration for the outer diameter of the distal end of the syringe adapter is the impact of inserting the distal end of the syringe adapter into the rubber membrane affixed to the top of the bottle. It is noted that some vendors state (for example, in a label affixed to a medicine bottle or perhaps in its accompanying literature) an upper limit on the number of times the rubber membrane can safely be punctured. An example is commercially known, for example, in which the label states that the rubber membrane should not be punctured more than 20 times. This limit is believed to be due to a potentially compromising effect that the puncturing tip of a sharp needle may have on the rubber membrane (where, for example, compromising the rubber membrane may enable the fluid medication to leak out). In view of this consideration, experimentation and testing was performed using prototypes with different sizes for the outer diameter of the distal end of the syringe adapter to determine what outer diameter size might compromise the rubber membrane. In this testing, the distal end of each tested prototype syringe adapter was cylindrical in shape.

For the testing of rubber membrane compromise, it was noted above that a common diameter of the rubber membrane fitted in the top of 250 ml bottles and 500 ml bottles is 0.75 inches. The typical rubber membrane has a dimple in the center where it is intended for the rubber membrane to be penetrated. A common size of this dimple is about 0.1730 inches to about 0.1760 inches. In view of this 0.75 inch membrane size and approximately 0.1750 inch dimple size, an initial test was conducted with a syringe adapter prototype having an outer diameter of approximately 0.26 inches on the distal end. Inserting this prototype through the rubber membrane was extremely difficult, and appeared to compromise the rubber membrane. Accordingly, no further testing above this 0.26 inch outer diameter was deemed beneficial. Another prototype syringe adapter was tested, this time having an outer diameter of 0.1815 inches on the distal end. Inserting this prototype into the rubber membrane was possible with less effort, and did not appear to compromise the rubber membrane. In view of these results, an upper bound on the outer diameter of the distal end of the syringe adapter is preferably about 0.1815 inches for a rubber membrane sized at about 0.75 inches and a corresponding dimple of about 0.1750 inches. In a more general case, an upper bound on the outer diameter of the distal end of the syringe adapter is approximately about the size of the dimple of the rubber membrane.

As has been demonstrated, an embodiment of the present invention improves syringeability of higher-viscosity medications, allowing such medication to be withdrawn from a bottle in much less time as compared to the known approach of withdrawal using a needle. More animals may therefore be medicated in a given period of time, leading to improved productivity of persons caring for the animals as well as enabling overall improved health for the animals. No longer will higher viscosity be a barrier to the market, and because medication of this type will be more readily administered when using a syringe adapter as disclosed herein, improvement may be expected in animal health, and market share and/or market presence for the medication may improve as well.

It should be noted that various features discussed herein with reference to "an embodiment", "one embodiment", "a preferred embodiment", and so forth should not be construed as suggesting that each such feature is present in a single embodiment, or in every embodiment, of the present invention. Instead, it should be understood that there may be various combinations of the disclosed features present in any particular embodiment.

While embodiments of the present invention have been described, additional variations and modifications in those embodiments may occur to those of ordinary skill in the art once they learn of the basic inventive concepts. Therefore, it is intended that the appended claims shall be construed to include the described embodiments and all such variations and modifications as fall within the spirit and scope of the invention.

The invention claimed is:

1. A syringe adapter threadably connectable to a syringe having a barrel and a syringe tip, the syringe tip located at a distal end of the syringe and having a syringe tip opening in a protrusion extending distally therefrom, the syringe tip configured with an internal threaded portion and the syringe tip opening providing entry into the barrel, the syringe adapter comprising:
a sidewall extending between a proximal end and a distal end opposite of the proximal end, the sidewall having an interior surface defining a chamber, the distal end of the sidewall being a distal end of the syringe adapter, the distal end of the syringe adapter being frustoconical in exterior shape and the interior surface of the distal end of the sidewall defining a distal end of the chamber as being frustoconical tapering toward the distal end of the syringe adapter, a terminal edge of the distal end of the sidewall defining a first opening into the chamber and a terminal edge of the proximal end of the sidewall defining a second opening into the chamber, the second opening sized to receive the protrusion and being a widest portion of the chamber, the first opening having an inner diameter of at least 0.05 inches; and
a flanged area extending outwardly from the terminal edge of the proximal end of the sidewall to threadably connect the syringe adapter to the internal threaded portion of the syringe tip and to thereby receive the protrusion into the chamber through the second opening, wherein:
a fluid communication path extends through the chamber, between the first opening and the second opening;
the distal end of the sidewall is configured for inserting into a container through a membrane covering an entry thereto, to thereby provide entry into the fluid communication path, through the first opening, for fluid medication to enter from the container into the chamber; and
the second opening provides an exit from the fluid communication path for the fluid medication to exit from the chamber, through the syringe tip opening and into the barrel of the syringe.

2. The syringe adapter according to claim 1, wherein a viscosity of the fluid medication is between 50 centipoise units and 350 centipoise units when a temperature of the fluid medication is at least 5 degrees Celsius.

3. The syringe adapter according to claim 1, further comprising a radial extension member that extends perpendicularly and radially outward from an exterior surface of the sidewall of the syringe adapter.

4. The syringe adapter according to claim 1, wherein the syringe adapter further comprises a multi-sided extension member that extends perpendicularly outward from an exterior surface of the sidewall of the syringe adapter.

5. The syringe adapter according to claim 1, wherein an inner shape of the syringe adapter tapers from the proximal end toward the distal end of the sidewall, for at least a portion of a length of the proximal end, at approximately 6 percent.

6. The syringe adapter according to claim 1, wherein a length of the sidewall, from the distal end of the sidewall to the proximal end, is between ⅜ inch and 2 inches.

7. The syringe adapter according to claim 1, wherein the inner diameter is between 0.078 inches and 0.14 inches.

8. The syringe adapter according to claim 1, wherein the inner diameter is between 0.09 inches and 0.11 inches.

9. The syringe adapter according to claim 1, wherein the syringe adapter threadably connects to the internal threaded portion of the syringe tip using a Luer-type lock connection.

10. A system for syringing higher-viscosity fluid medication, comprising:
   a syringe, the syringe comprising a barrel and a syringe tip, the syringe tip located at a distal end of the syringe and having a syringe tip opening in a protrusion extending distally therefrom, the syringe tip comprising a needle-attachment point, the needle-attachment point formed as an internal threaded portion of the syringe tip and the syringe tip opening providing entry into the barrel; and
   a syringe adapter comprising a sidewall extending between a proximal end and a distal end opposite of the proximal end, the sidewall having an interior surface defining a chamber, the distal end of the sidewall being a distal end of the syringe adapter, the distal end of the syringe adapter being frustoconical in exterior shape and the interior surface of the distal end of the sidewall defining a distal end of the chamber as being frustoconical tapering toward the distal end of the syringe adapter, a terminal edge of the distal end of the sidewall defining a first opening into the chamber and a terminal edge of the proximal end of the sidewall defining a second opening into the chamber, the second opening sized to receive the protrusion and being a widest portion of the chamber, the first opening having an inner diameter of at least 0.05 inches, wherein:
      a flanged area extending outwardly from the terminal edge of the proximal end of the sidewall threadably connects the syringe adapter to the internal threaded portion of the syringe tip and thereby receives the protrusion into the chamber through the second opening;
      a fluid communication path extends through the chamber, between the first opening and the second opening;
      the distal end of the sidewall is configured for inserting into a container through a membrane covering an entry thereto, to thereby provide entry into the fluid communication path, through the first opening, for the fluid medication to enter from the container into the chamber; and
      the second opening provides an exit from the fluid communication path for the fluid medication to exit from the chamber, through the syringe tip opening and into the barrel of the syringe.

11. The system according to claim 10, wherein the syringe is configured as one of a tab-handled syringe and a pistol-grip syringe.

12. The system according to claim 10, wherein the inner diameter is between 0.078 inches and 0.14 inches.

13. The system according to claim 10, wherein the inner diameter is between 0.09 inches and 0.11 inches.

14. The system according to claim 10, wherein a viscosity of the fluid medication is greater than or equal to 50 centipoise units when a temperature of the fluid medication is at least 5 degrees Celsius.

15. A syringe adapter threadably connectable to a syringe and through which viscous fluid medication can be flowed from a container to the syringe, the syringe adapter comprising:
   a sidewall, the sidewall having a proximal end, an opposite distal end, and an interior surface defining an interior chamber extending from the proximal end to the opposite distal end, the distal end of the sidewall being a distal end of the syringe adapter, the distal end of the sidewall terminating in a hollow frustoconical tip tapering toward the distal end of the syringe adapter, a terminal edge thereof defining a first opening into the interior chamber and a terminal edge at the proximal end of the sidewall defining a second opening into the interior chamber, the second opening being a widest portion of the interior chamber;
   a flanged area extending outwardly from the terminal edge of the proximal end, the flanged area comprising at least one tab configured to threadably engage a threaded interior portion of a syringe tip formed as a needle-attachment point on a distal end of the syringe; and
   a viscous fluid flow path extending through the interior chamber, between the first opening and the second opening, the first opening having an inner diameter of at least 0.05 inches, the first opening providing an entry point through which the viscous fluid medication enters into the interior chamber from the container upon inserting the frustoconical tip into the container through a membrane covering entry thereto, the viscous fluid flow path providing a path through the interior chamber to the second opening, the second opening providing an exit point for the viscous fluid medication to exit the syringe adapter and to enter the syringe, through an opening in the syringe tip, into a barrel of the syringe.

16. The syringe adapter according to claim 15, wherein a length of the syringe adapter, from the distal end of the sidewall to the proximal end, is between ⅜ inch and 2 inches.

17. The syringe adapter according to claim 15, wherein a viscosity of the viscous fluid medication is greater than or equal to 50 centipoise units when a temperature of the viscous fluid medication is at least 5 degrees Celsius.

18. The syringe adapter according to claim 15, wherein a shape of the interior chamber tapers from the proximal end of the sidewall toward the distal end of the sidewall, for at least a portion of a length of the proximal end of the sidewall, at 6 percent.

19. The syringe adapter according to claim 15, wherein the inner diameter is between 0.078 inches and 0.14 inches.

20. The syringe adapter according to claim 15, wherein the inner diameter is between 0.09 inches and 0.11 inches.

* * * * *